United States Patent
Ben-Yishai et al.

(10) Patent No.: US 10,932,689 B2
(45) Date of Patent: *Mar. 2, 2021

(54) MODEL REGISTRATION SYSTEM AND METHOD

(71) Applicant: ELBIT SYSTEMS LTD., Haifa (IL)

(72) Inventors: Rani Ben-Yishai, Haifa (IL); Lior Barak, Haifa (IL)

(73) Assignee: Elbit Systems Ltd., Haifa (IL)

( * ) Notice: Subject to any disclaimer, the term of this patent is extended or adjusted under 35 U.S.C. 154(b) by 291 days.

This patent is subject to a terminal disclaimer.

(21) Appl. No.: 16/036,629

(22) Filed: Jul. 16, 2018

(65) Prior Publication Data

US 2018/0317803 A1 Nov. 8, 2018

Related U.S. Application Data

(63) Continuation of application No. 15/531,685, filed as application No. PCT/IL2015/051160 on Nov. 29, 2015, now Pat. No. 10,022,065.

(30) Foreign Application Priority Data

Nov. 30, 2014 (IL) .......................... 236003

(51) Int. Cl.
*A61B 5/00* (2006.01)
*A61B 5/055* (2006.01)
(Continued)

(52) U.S. Cl.
CPC .............. *A61B 5/055* (2013.01); *A61B 34/10* (2016.02); *A61B 34/20* (2016.02);
(Continued)

(58) Field of Classification Search
CPC ......... A61B 5/055; A61B 34/10; A61B 34/20; A61B 2034/107; A61B 2034/2051; A61B 2034/2055

See application file for complete search history.

(56) References Cited

U.S. PATENT DOCUMENTS 6,259,943 B1  7/2001 Cosman et al.
6,529,765 B1  3/2003 Franck
(Continued)

FOREIGN PATENT DOCUMENTS

DE      10161787      7/2003
DE   102005045706    4/2007
(Continued)

OTHER PUBLICATIONS

International Search Report and Written Opinion dated Mar. 27, 2016 for International Application No. PCT/IL2015/051160, 9 pages.
(Continued)

*Primary Examiner* — Joel Lamprecht
(74) *Attorney, Agent, or Firm* — Knobbe, Martens, Olson & Bear LLP

(57) ABSTRACT

System for registering a coordinate system associated with a pre-acquired model of an object with a reference coordinate system. The system includes a portable unit which includes a display, a tracking system for tracking the portable unit and a processor. The processor is coupled with the portable unit and with the tracking system. The processor determines the position and orientation of the portable unit. The processor further determines the position of at least one marker located on the object according to at least one of, a tracked pointer and respective position related information. The processor further displays registration related information on the display. At least one of the registration related information and the display location of the registration related information are related to the position and orientation of the portable unit. The position of the at least one marker, in the coordinate system associated with the pre-acquired model, is predetermined.

30 Claims, 17 Drawing Sheets

(51) Int. Cl.
*A61B 34/10* (2016.01)
*A61B 34/20* (2016.01)

(52) U.S. Cl.
CPC . *A61B 2034/107* (2016.02); *A61B 2034/2051* (2016.02); *A61B 2034/2055* (2016.02)

(56) References Cited

U.S. PATENT DOCUMENTS

| | | |
|---|---|---|
| 6,640,127 B1 | 10/2003 | Kosaka et al. |
| 7,313,430 B2 | 12/2007 | Urquhart et al. |
| 7,556,428 B2 | 7/2009 | Sukovic et al. |
| 7,671,887 B2 | 3/2010 | Pescatore et al. |
| 7,747,312 B2 | 6/2010 | Barrick et al. |
| 7,920,909 B2 | 4/2011 | Lyon et al. |
| 8,010,177 B2 | 8/2011 | Csavoy et al. |
| 8,238,631 B2 | 8/2012 | Hartmann et al. |
| 8,380,288 B2 | 2/2013 | Labadie et al. |
| 8,392,022 B2 | 3/2013 | Ortmaier et al. |
| 8,483,434 B2 | 7/2013 | Buehner et al. |
| 8,657,809 B2 | 2/2014 | Schoepp |
| 10,022,065 B2 * | 7/2018 | Ben-Yishai ............ A61B 34/20 |
| 2003/0055410 A1 | 3/2003 | Evans |
| 2003/0210812 A1 | 11/2003 | Khamene et al. |
| 2005/0015005 A1 | 1/2005 | Kockro |
| 2008/0119712 A1 | 5/2008 | Lloyd et al. |
| 2008/0306378 A1 | 12/2008 | Trousset et al. |
| 2008/0319491 A1 | 12/2008 | Schoenefeld et al. |
| 2010/0039506 A1 | 2/2010 | Sarvestani et al. |
| 2011/0009855 A1 | 4/2011 | Robbins et al. |
| 2011/0085720 A1 | 4/2011 | Averbuch |
| 2011/0098553 A1 | 4/2011 | Robbins et al. |
| 2012/0004541 A1 | 1/2012 | Yamamoto et al. |
| 2012/0007823 A1 | 1/2012 | Ozawa et al. |
| 2013/0060146 A1 | 3/2013 | Yang |
| 2013/0322719 A1 | 12/2013 | Dekel et al. |
| 2014/0005527 A1 | 1/2014 | Nagarkar et al. |
| 2014/0049629 A1 | 2/2014 | Siewerdsen |
| 2014/0107471 A1 | 4/2014 | Haider |
| 2016/0015471 A1 | 1/2016 | Piron |

FOREIGN PATENT DOCUMENTS

| | | |
|---|---|---|
| DE | 102007013535 A1 | 9/2008 |
| EP | 1524626 | 4/2005 |
| EP | 1873666 A1 | 3/2009 |
| EP | 1800616 | 7/2011 |
| WO | WO 98/38908 A1 | 9/1998 |
| WO | WO 01/54558 A2 | 8/2001 |
| WO | WO 02/35454 A1 | 5/2002 |
| WO | WO 03/026505 A1 | 4/2003 |
| WO | WO 2006/027201 A1 | 3/2006 |
| WO | WO 2007/136745 A1 | 1/2008 |
| WO | WO 2008082574 A1 | 7/2008 |
| WO | WO 2008/130354 A1 | 10/2008 |
| WO | WO 2008/130355 A1 | 10/2008 |
| WO | WO 2008/130361 A1 | 10/2008 |
| WO | WO 2010/124672 A1 | 11/2010 |
| WO | WO 2011/134083 A1 | 11/2011 |
| WO | WO 2012/033552 A1 | 3/2012 |

OTHER PUBLICATIONS

"Marker Tracking and HMD Calibration for a Video-Based Augmented Reality Conferencing System", Hirokazu Kato and Mark Billinghurst, In Proceedings of the 2nd IEEE and ACM International Workshop on Augmented Reality (IWAR '99) 1999, IEEE Computer Society, Washington, DC, USA, pp. 85-94, Oct. 1999.

"Fast color fiducial detection and dynamic workspace extension in video see-through self-tracking augmented reality", Youngkwan Cho, Jun Park, and U. Neumann, In Proceedings of the 5th Pacific Conference on Computer Graphics and Applications (PG '97) 1997, IEEE Computer Society, Washington, DC, USA, pp. 168-177, Oct. 1997.

* cited by examiner

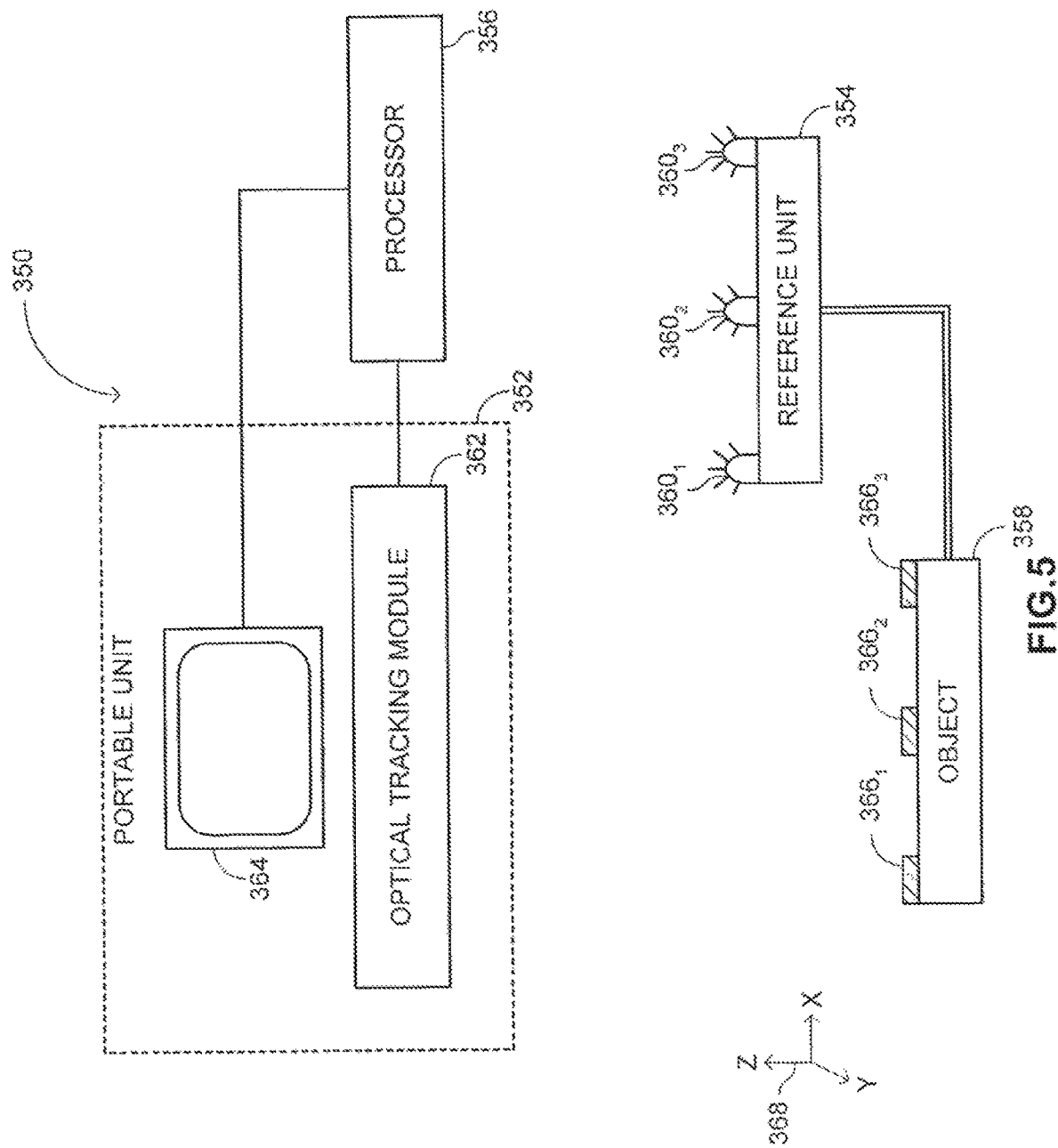

```
┌─────────────────────────────────────────────────────────────┐
│ DETERMINING THE POSITION OF EACH OF AT LEAST THREE MARKERS IN A │
│ COORDINATE SYSTEM ASSOCIATED WITH A MODEL OF AN OBJECT, AT  │
│ LEAST ONE OF SAID AT LEAST THREE MARKERS IS A FIDUCIAL MARKER │
└─────────────────────────────────────────────────────────────┘
                                                        ⟍ 450

┌─────────────────────────────────────────────────┐
        │ DETERMINING THE POSITION OF AT LEAST ONE ANATOMICAL │
        │ LANDMARK IN THE REFERENCE COORDINATE SYSTEM WHEN THE AT │
        │ LEAST ONE ANATOMICAL LANDMARK IS EMPLOYED AS ONE OF THE AT │
        │ LEAST THREE MARKERS                             │
        └─────────────────────────────────────────────────┘
                                                        ⟍ 452

┌─────────────────────────────────────────────────┐
        │ FOR EACH OF AT LEAST ONE REGISTRATION POSITION  │
        │ DETERMINING THE POSITION AND ORIENTATION OF A PORTABLE │
        │ UNIT IN A REFERENCE COORDINATE SYSTEM, THE PORTABLE │
        │ UNIT INCLUDING AN OPTICAL DETECTION ASSEMBLY    │
        └─────────────────────────────────────────────────┘
                                                        ⟍ 454

┌─────────────────────────────────────────────────┐
        │ FOR EACH OF THE AT LEAST ONE REGISTRATION POSITION, │
        │ DETERMINING POSITION RELATED INFORMATION RESPECTIVE │
        │ OF EACH OF THE AT LEAST ONE FIDUCIAL MARKER THAT ARE │
        │ WITHIN THE FIELD OF VIEW OF THE OPTICAL DETECTION │
        │ ASSEMBLY                                        │
        └─────────────────────────────────────────────────┘
                                                        ⟍ 456

┌─────────────────────────────────────────────────┐
        │ DETERMINING THE POSITION OF EACH OF THE AT LEAST ONE │
        │ FIDUCIAL IN THE REFERENCE COORDINATE SYSTEM ACCORDING │
        │ TO THE RESPECTIVE POSITIONS AND ORIENTATIONS OF THE │
        │ PORTABLE UNIT IN EACH OF THE AT LEAST ONE REGISTRATION │
        │ POSITIONS AND THE RESPECTIVE POSITION RELATED   │
        │ INFORMATION                                     │
        └─────────────────────────────────────────────────┘
                                                        ⟍ 458

┌─────────────────────────────────────────────────────────────┐
│ REGISTERING THE COORDINATE SYSTEM ASSOCIATED WITH THE MODEL │
│ OF THE OBJECT WITH THE REFERENCE COORDINATE SYSTEM ACCORDING │
│ TO THE RESPECTIVE POSITIONS OF THE AT LEAST THREE MARKERS IN │
│ BOTH COORDINATE SYSTEMS                                     │
└─────────────────────────────────────────────────────────────┘
                                                        ⟍ 460
```

FIG. 8

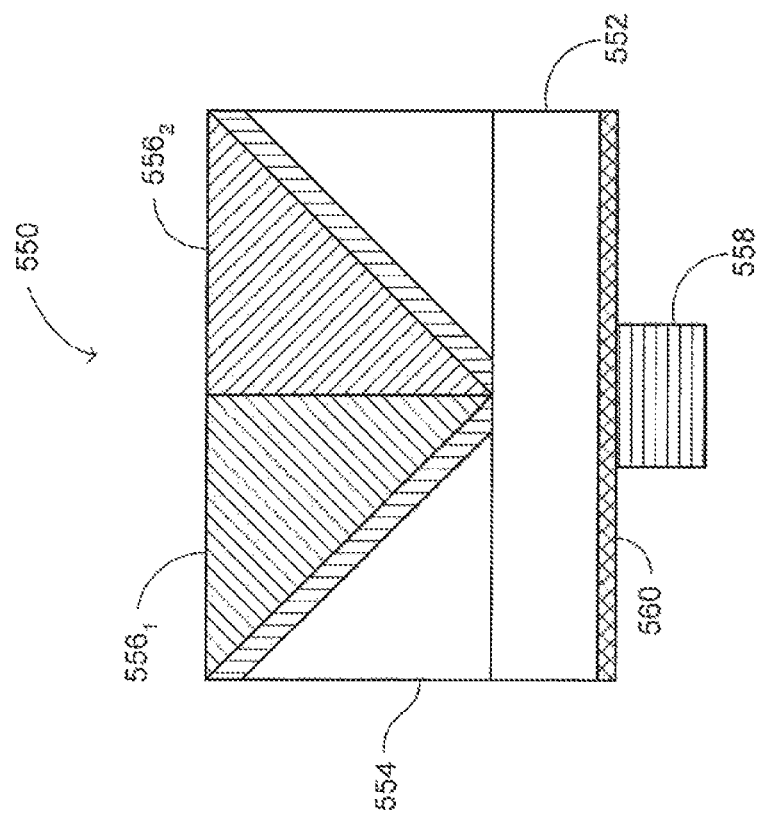

MODEL REGISTRATION SYSTEM AND METHOD

CROSS REFERENCE TO RELATED APPLICATIONS

This application is a Continuation Application of U.S. patent application Ser. No. 15/531,685, filed on May 30, 2017, issued as U.S. Pat. No. 10,022,065 issued on Jul. 17, 2018, which is the U.S. National Phase Application under 35 U.S.C. § 371 of International Application No. PCT/IL2015/051160, filed Nov. 29, 2015, which claims priority to Israeli Application No. 236003, filed on Nov. 30, 2014, the entire disclosure of each of which is hereby incorporated by reference.

FIELD OF THE DISCLOSED TECHNIQUE

The disclosed technique relates to tracking systems in general, and to system and methods for registering a model of an object with a reference coordinate system associated with a tracking system, in particular.

BACKGROUND OF THE DISCLOSED TECHNIQUE

Registering the coordinate system associated with an image of the patient with the coordinate system associated with a medical tracking system enables the display of intraoperative information, (e.g., a representation of a medical tool, navigational information) on the image of a body part of interest of a patient, at the respective positions and orientations thereof. Thus, the user may see such intraoperative information along with the patient body part of interest.

U.S. Patent Application Publication U.S. 2011/0098553 to Robbins et al directs to an automatic registration of a Magnetic Resonance (MR) image with an image guidance system. The registration is achieved by placing MR visible markers at known positions relative to markers visible in a camera tracking system. The markers are fixed to a common fixture which is attached to a head clamp together with a reference marker (employed when the markers are covered or removed). The tracking system includes a camera with a detection array for detecting visible light and a processor arranged to analyze the output from the array. Each object to be detected carries a single marker with a pattern of contrasted areas of light and dark intersecting at a specific single feature point thereon with an array around the specific location. This enables the processor to detect an angle of rotation of the pattern and to distinguish each marker from the other markers.

U.S. Patent Application Publication 2012/0078236 to Schoepp, directs to a method for automatically registering the coordinate system associated with a navigation system with a coordinate system associated with a scan image. Initially, a camera assembly of a navigation system, which includes fiducial markers, is fixedly attached to the patient (e.g., with an adhesive). Thereafter, a scan image of the patient with the camera is acquired. Scan image includes the camera with the fiducial markers. The registration module automatically recognizes and identifies the fiducial markers visible in the scan image and determines the position of the camera assembly therefrom (i.e., the position of the fiducial markers with respect to the camera coordinate system and to the focal geometry of the camera are known). The registration module automatically registers the camera space with respect to the position of the patient in the scan image by identifying the position of the camera coordinate system within the scan image. Upon automatic registration of the camera, the tracking of a surgical tool is immediately available through the known relationships between the surgical tool, the camera coordinate system, the scan image coordinate system.

SUMMARY OF THE PRESENT DISCLOSED TECHNIQUE

It is an object of the disclosed technique to provide a novel method and system for registering a model of an object with a reference coordinate system associated with a tracking system, in particular In accordance with the disclosed technique, there is thus provided a system for registering a coordinate system associated with a model of an object with a reference coordinate system associated with the object. The system includes a portable unit, a tracking system and a processor. The portable unit includes a display. The processor is coupled with the portable unit and with the tracking system. The tracking system tracks the portable unit in the reference coordinate system. The processor determines the position and orientation of the portable unit in the reference coordinate system. The processor further determines the position of at least one marker located on the object in the reference coordinate system according to at least one of, a tracked pointer and respective position related information. The processor also displays registration related information on the display, at least one of the registration related information and the display location of the registration related information being related to the position and orientation of the portable unit in the reference coordinate system.

In accordance with another aspect of the disclosed technique, there is thus provided method for displaying registration related information comprising the procedures of determining the position of markers in a coordinate system associated with a model of an object, the markers being located on the object and determining the position and orientation of a portable unit in a reference coordinate system, the portable unit including a display. The method further includes the procedures of determining the position of at least three of the markers in a reference coordinate system and registering the coordinate system associated with a model of the object with the reference coordinate system according to the respective determined positions of the at least three of the markers, in both coordinate systems. The method also includes the procedure of displaying registration related information on the display, at least one of the registration related information and the display location of the registration related information being related to the position and orientation of the portable unit in the reference coordinate system.

BRIEF DESCRIPTION OF THE DRAWINGS

The disclosed technique will be understood and appreciated more fully from the following detailed description taken in conjunction with the drawings in which:

FIG. 5 is a schematic illustration of an optical tracking system, which tracks the location of the portable unit in a reference coordinate system, constructed and operative in accordance with a further embodiment of the disclosed technique;

FIG. 8 is a schematic illustration of a method for registering a model coordinate system and a reference coordinate system in accordance with another embodiment of the disclosed technique;

FIG. 10 is a schematic illustration of cross-sectional view of a passive registration marker, constructed and operative in accordance with another embodiment of the disclosed technique.

DETAILED DESCRIPTION OF THE EMBODIMENTS

Figure 1A:
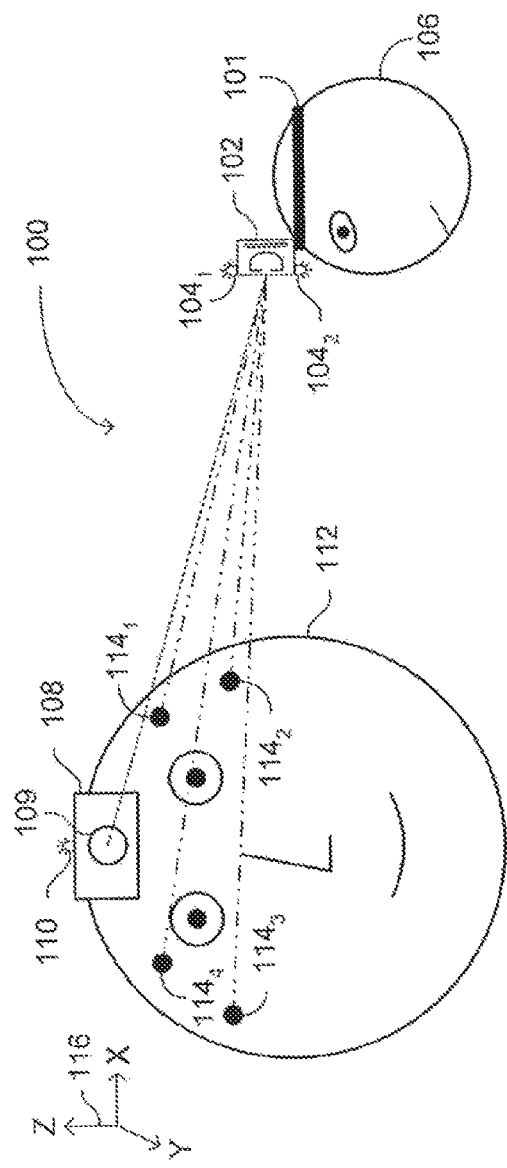
FIGS. 1A, 1B and 1C are schematic illustrations of an exemplary method for determining the location of fiducial markers located on an object, in accordance with an embodiment of the disclosed technique.

The disclosed technique overcomes the disadvantages of the prior art by providing a novel system and method for registering a model of an object with a reference coordinate system associated with a tracking system. The tracking system may be an optical tracking system, an electromagnetic tracking system, an ultrasonic tracking system, an optical Time-Of-Flight tracking system. According to the disclosed technique, the tracking system tracks the position and orientation of a portable unit in the reference coordinate system. The portable unit includes an optical detection assembly (e.g., sensor array camera, a Position Sensitive Device—PSD, a stereoscopic camera or a Time-Of-Flight camera). Prior to the registration process a model of the object (e.g., a 2D or a 3D image of the head of the patient) is determined. Furthermore, the locations of at least three markers (i.e., fiducials or anatomical landmarks) are determined in the coordinate system associated with the model.

During the registration process, in order to determine the location of fiducial markers in the reference coordinate system, the portable unit is held at a distance from the object. The user moves the portable unit around the object through at least one registration positions. Each registration position is associated with a respective viewing angle of the fiducial. For example when the optical detection assembly of the portable unit includes an optical detector (e.g., sensor array camera or a PSD), then, the number of registration positions is at least two. When the optical detection assembly of the portable unit includes a stereoscopic camera or a TOF camera, the number of registration positions is at least one. For each registration position, the tracking system determines the position and orientation (P&O) of the portable unit in the reference coordinate system. Substantially simultaneously therewith, for each registration position, the tracking system determines position related information respective of each fiducial according to the acquired image of the fiducial. When the portable unit includes an optical detector (e.g., Charged Coupled Device—CCD camera or a Complementary Metal Oxide Semiconductor—CMOS camera or a PSD), the position related information includes a respective directions toward each of the at least one fiducial marker located on the object. Each direction defines a line in the reference coordinate system. The intersection of the at least two lines associated with each fiducial (i.e., a line for each registration position), defines the location of that fiducial in the reference coordinate system. When the portable unit includes, for example, a stereoscopic camera or a TOF camera, the position related information may be related directly to the position of the fiducial in the reference coordinate system (e.g., two directions from the two detectors in the stereoscopic camera or pixel depth information from the TOF camera). Also, the location of the markers (i.e., either of the fiducial markers or of the anatomical landmarks) may be determined with a pointer which is tracked in the reference coordinate system. Since the coordinates of the markers in the coordinate system associated with the model are known, the system can determine the correspondence between the location of the markers in the referenced coordinate system and the location of the markers in the model coordinate system. Thus, registration between the coordinate system associated with the model and the coordinate system associated with the tracking system is achieved. Furthermore, the portable unit may include a display. Also, herein, the term 'located marker' refers to a marker that the position thereof in the reference coordinate system was determined.

When the tracking system is an optical tracking system, the tracking system may exhibit an in-out configuration, an in-out-out-in configuration or an out-in configuration. In the in-out configuration, the portable unit includes at least one optical detector, and a reference unit, which is at a fixed position and orientation relative to the object being tracked, includes at least three light emitters. In the out-in configuration the portable unit includes at least three light emitters, and a reference unit includes at least one optical detector. In the in-out-out-in configuration the optical tracking system includes at least two optical detectors, one located on the portable unit and the other is located on a reference unit. Further in the in-out-out-in configuration, at least one light emitter is located on one of the portable unit and the reference unit and at least two light emitters are located on the other one of the portable unit and the reference unit (i.e., a total of at least three light emitters are employed). In both the in-out configuration and the in-out-out-in configuration, an optical detector may be located on the portable unit and employed for both tracking and marker detection (i.e., during the registration process).

In a tracking system employed for registration according to the disclosed technique, the position and orientation of the reference unit are fixed relative to a patient body part. For example, the reference unit is directly fixed to the patient body part. According to another example, the patient body part is fixed and the reference unit is also fixed, thus the reference unit is at fixed position and orientation relative to the patient body part without being attached thereto. The disclosed technique may also be employed in other augmented reality scenarios.

Initially, prior to the registration procedure, a model of the patient is determined. This model may be, for example, a two-dimensional or three-dimensional image of a region of interest of the body of the patient (e.g., X-ray image, computed tomography—CT image, Magnetic Resonance Imaging—MRI image, ultrasound image, Proton Emission Tomography—PET image and the like). The model may be acquired pre-operatively or intra-operatively. The model includes representations of the at least three markers, which are employed as location points of reference during registration of the coordinate systems. As mentioned above, these markers may be artificial markers (i.e., fiducials) which are attached to the patient prior to the acquisition of the model and remain attached to the patient until and during the registration procedure and optionally during the medical procedure which follows. Alternatively or additionally the markers may be anatomical landmarks which are visible in the model (e.g., the nose bridge or the tragus in the ear). The location coordinates of these markers in the model coordinate system are determined by employing image processing techniques or by manual localization on the image (e.g., with the aid of a cursor).

Figure 1B:
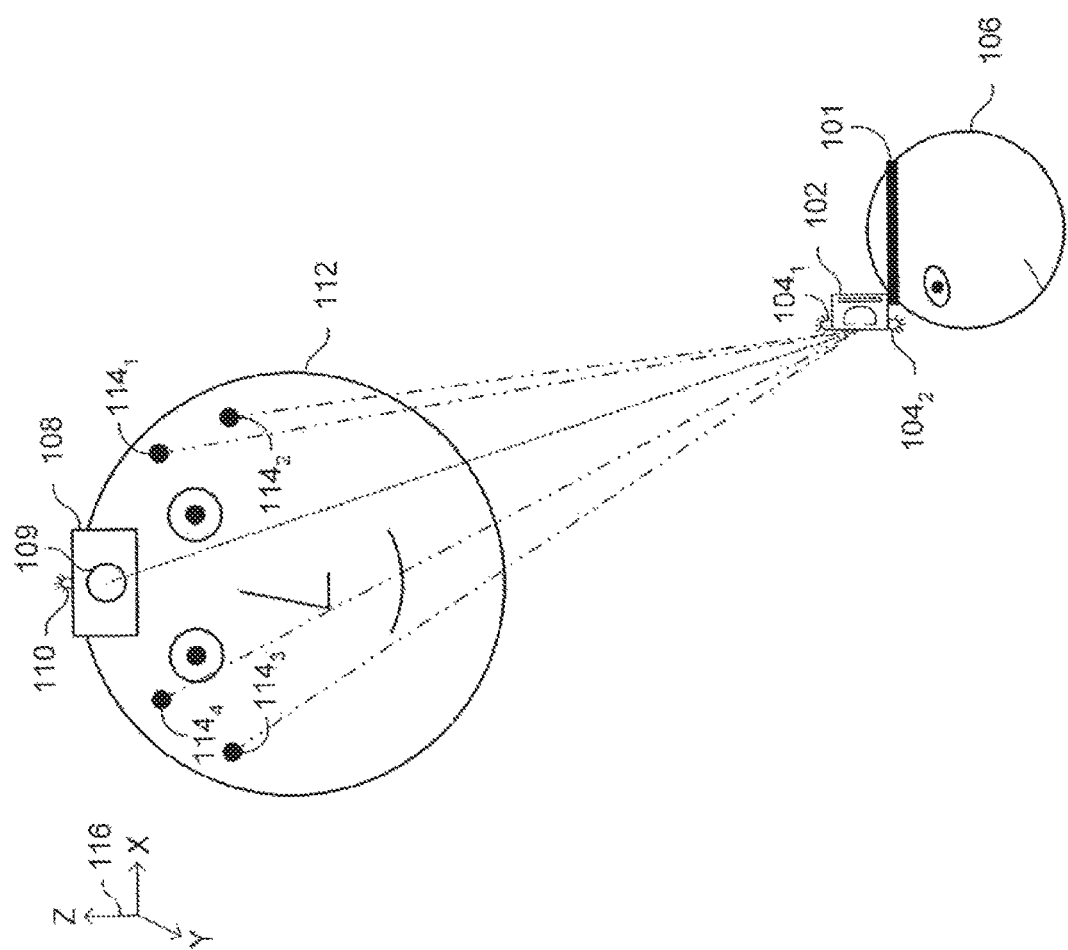
Figure 1C:
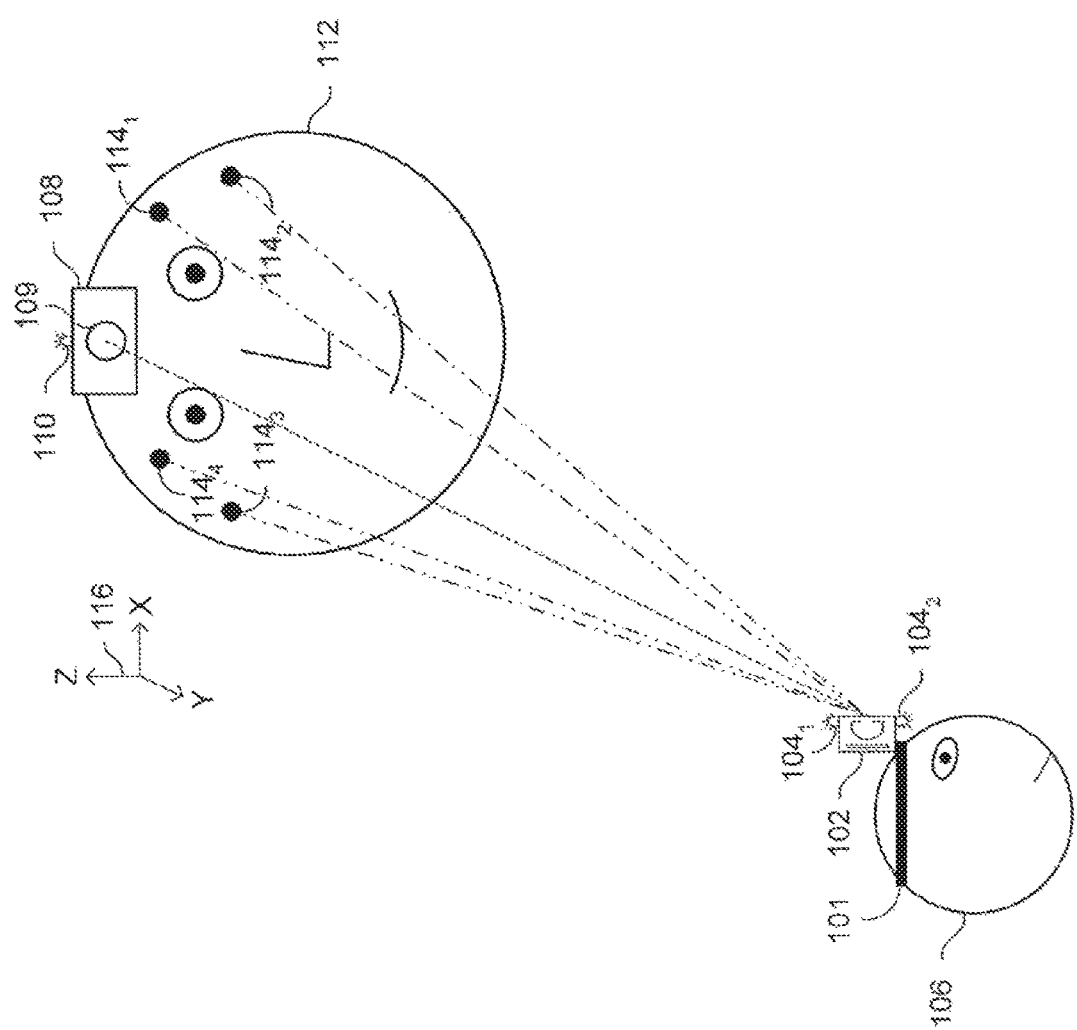

Thereafter, and prior to the medical procedure, the locations of the markers in the reference coordinate system associated with the tracking system are determined. Reference is now made to FIGS. 1A, 1B and 1C which are schematic illustrations of an exemplary method for determining the location of fiducial markers located on an object for the purpose of registering the coordinate system associated with a model of the object, with a coordinate system associated with a tracking system, generally referenced 100, in accordance with an embodiment of the disclosed technique. Tracking system 100 in FIGS. 1A, 1B and 1C is an optical tracking system which exhibits an in-out-out-in configuration. System 100 includes a reference unit 108 and a portable unit 101. Portable unit 101 includes a moving optical detector 102 associated with two light emitters $104_1$ and $104_2$. Reference unit 101 is located, for example, on the head of a user 106. Reference unit 108 includes a reference optical detector 109 associated with a light emitter 110. Reference unit 108, and thus light emitter 110 and optical detector 109 are in a fixed position and orientation relative to a body part of patient 112. In FIGS. 1A-1C reference unit 108 is located on the head of patient 112. In general, reference unit 108 may be fixed relative to the body part of the patient without being physically attached thereto. In other words reference unit 108 and the body part of patient 112 do not move one with respect to the other. In the example set forth in FIGS. 1A-1C optical detector 109 is a sensor array camera or a PSD. Thus, at least two registration positions are required.

To register the coordinate system associated with the model, with the coordinate system associated with the tracking system, the locations of the markers in the coordinate system associated with the tracking system should be determined. To that end, the tracking system determines the location of the markers in a reference coordinate system. Accordingly, with reference to FIG. 1A, user 106 views patient 112 from a first registration position. Moving optical detector 102 detects light emitter 110 and markers $114_1$, $114_2$, $114_3$ and $114_4$. Reference optical detector 109 detects light emitters $104_1$ and $104_2$. The processor determines the relative position and orientation between moving optical detector 102 and reference optical detector 109 at this first registration position, and thus the relative position and orientation between portable unit 101 and reference unit 108 in reference coordinate system 116. Reference coordinate system 116 is associated with reference unit 108. Furthermore, the processor determines a first direction from moving optical detector 102 toward each of markers $114_1$, $114_2$, $114_3$ and $114_4$, relative to moving optical detector 102, according to the representations of markers $114_1$, $114_2$, $114_3$ and $114_4$ detected by moving optical detector 102, as explained below.

With reference to FIG. 1B, user 106 views patient 112 from a second registration position. Moving optical detector 102 detects light emitter 110 and markers $114_1$, $114_2$, $114_3$ and $114_4$ from this second registration position and reference optical detector 108 detects light emitters $104_1$ and $104_2$ again. The processor determines the relative position and orientation between first detector 102 and reference unit 108 at this second registration position, and thus the relative position and orientation between portable unit 101 and reference unit 108, in reference coordinate system 116. Furthermore, the processor determines a second direction from moving optical detector 102 toward each of markers $114_1$, $114_2$, $114_3$ and $114_4$, relative to moving optical detector 102 according to the representations of markers $114_1$, $114_2$, $114_3$ and $114_4$ detected by moving optical detector 102.

With reference to FIG. 1C, user 104 views patient 112 from a third registration position. Moving optical detector 102 detects yet light emitter 110 and markers $114_1$, $114_2$, $114_3$ and $114_4$ from this third registration position and reference optical detector 108 detects light emitters $104_1$ and $104_2$ yet again. The processor determines the relative position and orientation between first detector 102 and reference unit 108 at this third registration position, and thus the relative position and orientation between portable unit 101 and reference unit 108, in reference coordinate system 116. Furthermore, the processor determines a third direction from moving optical detector 102 toward each of markers $114_1$, $114_2$, $114_3$ and $114_4$, relative to moving optical detector 102 according to the representations of markers $114_1$, $114_2$, $114_3$ and $114_4$ detected by moving optical detector 102.

The processor determines the location of each of markers $114_1$, $114_2$, $114_3$ and $114_4$ in reference coordinate system 116, according to the three directions associated with each one of marker $114_1$, $114_2$, $114_3$ and $114_4$. For example each direction defines a line in reference coordinate system 116 and the intersection of these three lines, associated with each marker, defines the location of that marker in reference coordinate system 116. In practice, the three lines may not intersect due to measurement errors and noise. Thus, for example, the point in space which exhibits the minimum sum of distances from the three lines is determined as the location of the marker. Alternatively, for example, each determined direction may be associated with a Figure Of Merit (FOM) and each direction is weighted according to the FOM thereof.

The above description in conjunction with FIGS. 1A-1C described registering the coordinate system associated with the model, with the coordinate system associated with the tracking system by employing three different registration positions. However, in general, two registration positions are sufficient to determine the position of the markers in the reference coordinate system. Nevertheless, in practice, more than two registration positions are employed. For example, the registration system automatically selects a plurality of discreet points in time (e.g., according to how fast the user is moving), determines the position and orientation of the user in those points in time and determines a direction for each identified fiducial as described above. It is also noted that the portable unit may include two optical detectors directed substantially toward the same Field Of View (e.g., stereoscopic camera). Consequently, detecting a fiducial with each of the two detectors is sufficient from a single user position (i.e., assuming the fiducials are detected substantially simultaneously). Then, the system may triangulate the detected fiducial in order to determine the location thereof in the referenced coordinate system.

Furthermore, the above description in conjunction with FIGS. 1A-1C relates to fiducial markers (i.e., at least one of the markers is a passive or an active fiducials as further explained below), and the fiducial emits light (i.e., the fiducial includes either a light source or a light reflector) which can be detected by the optical detector in addition to being detected by the imaging machine, as further explained below.

The location of all or some of the markers (i.e., either fiducial markers or anatomical landmarks) may also be determined by employing a tracked pointer, as further explained below. For example, the user places the tip of the pointer on the marker and the tracking system determines the location of the tip of the pointer in the reference coordinate system (i.e., similar to as performed in manual registration). It is noted that if only a tracked pointer is employed to determine the location of the markers, than the portable unit need not include an optical detection assembly. Since the locations of the markers in the model coordinate system are known, the system can determine the correspondence between the location of the marker in the referenced coordinate system and the location of the markers in the model coordinate system. When a tracked pointer is employed, the portable unit does not need to move through registration positions as explained above.

Figure 2:
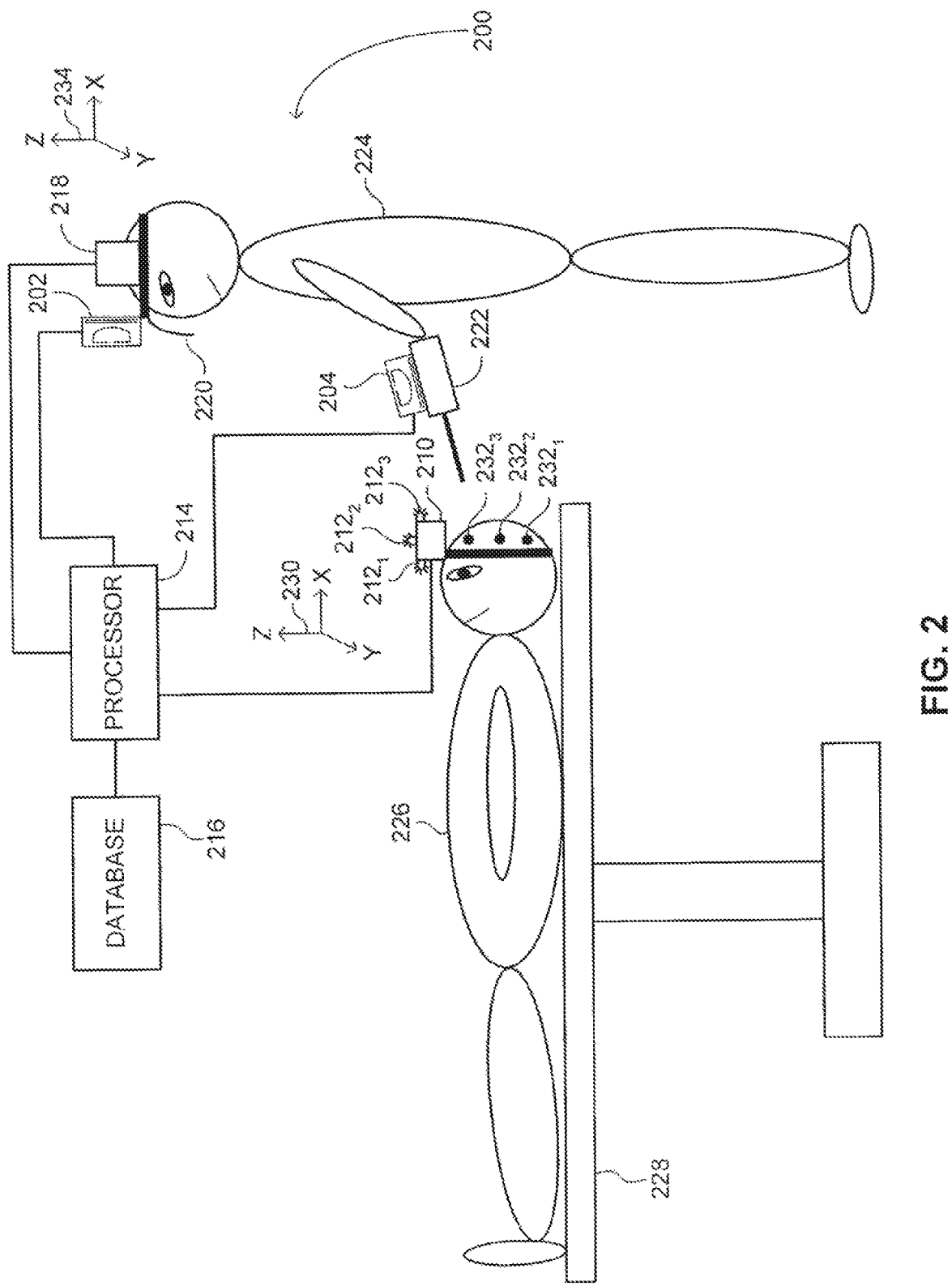
FIG. 2 is a schematic illustration of an exemplary optical tracking system for registering a coordinate system associated with a model of a patient body part with a coordinate system associated with a medical tracking system, in accordance with another embodiment of the disclosed technique.

Reference is now made to FIG. 2, which is a schematic illustration of an exemplary optical tracking system, generally reference 200, for registering a coordinate system associated with a model of a patient body part with a coordinate system associated with a medical tracking system, in accordance with another embodiment of the disclosed technique. System 200 may further be employed for tracking a medical tool in a reference coordinate system. The tool may be superimposed on a model of a patient 226. System 200 includes a first optical detector 202, a second optical detector 204 and a reference unit 210. Reference unit 210 further includes reference light emitters $212_1$, $212_2$ and $212_3$. System 200 further includes a processor 214, a database 216 and a display such as HMD 218. HMD 218 includes a visor 220. HMD 218 may also be in the form of near-eye-display. HMD 218 and first optical detector 202 define the portable unit. HMD 218 may also be replaced with a conventional screen (e.g., a hand-held tablet computer).

Processor 214 is coupled with database 216, first optical detector 202, HMD 218, second optical detector 204. When light emitters $206_1$ and $206_2$, or reference light emitters $212_1$, $212_2$ and $212_3$ are LEDs, processor 214 is optionally coupled therewith. HMD 218 along with first optical detector 202 and light emitters $206_1$ and $206_2$ is donned by a physician 224. Second optical detector 204 is attached to medical tool 222. Reference unit 210, along with reference light emitters $212_1$, $212_2$ and $212_3$ are all attached to a patient 226 body location (e.g., the head, the spine, the femur), or fixed relative thereto. Patient 226 is lying on treatment bed 228. In FIG. 2, the patient 226 body location is the head of patient 226. System 200 is associated with a reference coordinate system 230 which, in the system 200 is also the coordinate system associated with reference unit 210. In FIG. 2, the portable unit and reference unit 210 exhibit an in-out configuration. Furthermore, HMD 218 is associated with a respective coordinate system 234. Also, markers, such as markers $232_1$, $232_2$ and $232_3$, may be attached to patient 226. Although only three markers are depicted in FIG. 2, in general, similar to as described in FIGS. 1A-1C, more than three markers may be employed. Furthermore, at least one of markers $232_1$, $232_2$ and $232_3$ is a fiducial marker. Also, the remaining ones of markers $232_1$, $232_2$ and $232_3$ may be anatomical landmarks.

Processor 214 may be integrated within HMD 218 or attached to the user (e.g., with the aid of a belt or in the user's pocket). Medical tool 222 is, for example, a pointer employed for determining the location of the markers employed for registration. Medical tool 222 may also be an ultrasound imager, a medical knife, a catheter guide, a laparoscope, an endoscope, a medical stylus or any other tool used by a physician 224 during a procedure conducted on a patient 226. Also, the term coupled herein relates to either coupled by wire or wirelessly coupled.

In general, system 200 may be employed for registering the coordinate systems associated with a model of patient 226 with reference coordinate system 230 as well as for tracking medical tool 222. Similar to as described above, prior to registration, a model of the patient is determined which includes markers, such as marker $232_1$, $232_3$ and $232_3$. Markers $232_1$, $232_3$ and $232_3$ are employed as location points of reference during registration procedure and the location coordinates of these markers, in the model coordinate system are determined (i.e., employing image processing techniques or by manual localization on the model). This model, along with the location coordinates of the markers is then stored in database 216.

Thereafter, physician 224 moves through at least two registration positions. For each registration position, first optical detector 202 detects markers $232_1$, $232_2$ and $232_3$ and light emitters $212_1$, $212_2$ and $212_3$. For each registration position, processor 214 determines the position and orientation of HMD 218 (i.e., in reference coordinate system 230), according to the detected directions of light emitters $212_1$, $212_2$ and $212_3$ and the known locations of light emitters $212_1$, $212_2$ and $212_3$ on reference unit 210 (e.g., these locations are stored in database 216). Furthermore, for each registration position, processor 214 determines a respective direction from HMD 218 toward each of markers $232_1$, $232_2$ and $232_3$. Processor 214 determines the location of each of markers $232_1$, $232_2$ and $232_3$ according to the respective directions thereof at each registration position (e.g., the intersection of the lines defined by each respective direction, define a location point in reference coordinate system 230).

Also, physician 224 may employ a pointer to locate the markers (i.e., either the fiducial markers or the anatomical landmarks). In such a case medical tool 222 takes the form of a pointer. In order to determine the location of the markers, physician 224 places the tip of the pointer on the markers. Second optical detector 204 also acquires an image of light emitters $212_1$, $212_2$ and $212_3$ and processor 214 determines the location of the pointer (i.e., of medical tool 222), and thus of the marker, in reference coordinate system 230. Similar to as mentioned above, once processor 214 determines the position of the markers $232_1$, $232_2$ and $232_3$ (i.e., of the fiducials and the anatomical landmark) in reference coordinate system 230, processor 214 can register the coordinate system associated with the model of the body part of patient 226 with reference coordinate system 230.

When processor 214 determines at least an initial registration (e.g., registration with a relatively large error) the coordinate system associated with the model of the body part of patient 226 with reference coordinate system 230, processor 214 may display on visor 220 registration related information as further explained below. Once the coordinate system associated with the model of the body part of patient 226 is registered with reference coordinate system 230, tracking system 200 may be employed to track another medical tool (e.g., medical tool 222 takes the form of a needle) in reference coordinate system 230. Furthermore, tracking system can superimpose a representation of such a medical tool on the model of patient 222. Also, according to the determined relative positions and orientations between medical tool 222, HMD 218 and patient 226, and the registration between the model of patient 226 and reference coordinate system 230, processor 214 may render the model of patient 226 in the correct perspective and provide the rendered model to HMD 218. Furthermore, navigational information (e.g., a mark representing a target location, a line representing the trajectory and projected trajectory of the tool) associated with medical tool 222, may be superimposed on the model. As a further example, when medical tool 222 is an ultrasound imager, system 200 be employed for presenting data acquired by medical tool 222 at the location from which that data was acquired.

The light emitters described hereinabove in conjunction with FIGS. 1A-1C and 2 may be either active light emitters (e.g., LEDs) or passive light emitters which reflect either the ambient light or dedicated light directed thereat (e.g., the light from the LEDs located on the portable unit). The passive light emitters may be reflectors (e.g., reflective spheres) or retro-reflectors which reflect light toward the direction from which it impinged thereon. The fiducial markers described hereinabove in conjunction with FIGS. 1A-1C and 2 may also be passive fiducials or active fiducials. The passive fiducial also reflects the light impinging thereon. The active fiducial includes a LED and a battery and is activated just before the registration process starts as further explained below in conjunction with FIGS. 9C-9E and 11A.

Figure 3:
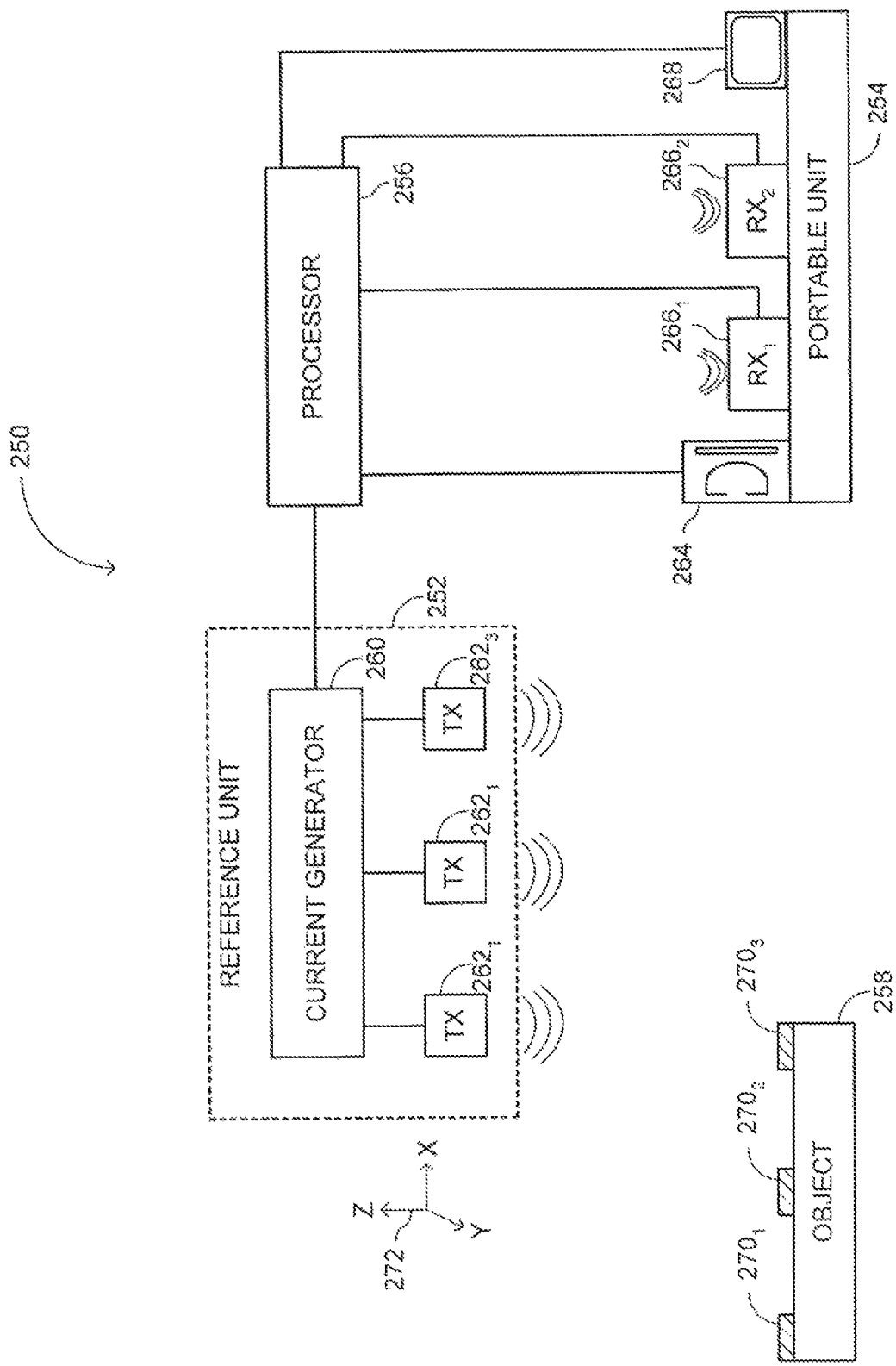
FIG. 3 is a schematic illustration of an exemplary electromagnetic tracking system employed for registering a model coordinate system with a reference coordinate system, constructed and operative in accordance with a further embodiment of the disclosed technique.

As mentioned above, the tracking system employed for registration may also be an electro-magnetic tracking system, which tracks the location of the portable unit in a reference coordinate system. Reference is now made to FIG. 3, which is a schematic illustration of an exemplary electromagnetic tracking system, generally referenced 250, employed for registering a model coordinate system with a reference coordinate system, constructed and operative in accordance with a further embodiment of the disclosed technique. System 250 includes a reference unit 252, a portable unit 254 and a processor 256. Reference unit 252 includes a current generator 260 and magnetic field transmitting elements (e.g., coils) $262_1$, $262_2$ and $262_3$. Portable unit 254 includes an optical detection assembly 264 and magnetic field receivers $266_1$ and $266_2$. Portable unit 254 also includes a display 268. Portable unit 254 may be embodied as an HMD similar to HMD 218 (FIG. 2) or a hand held unit (e.g., a hand-held tablet computer). Optical detection assembly 264 is for example sensor array camera, a PSD, a stereoscopic camera or a TOF camera.

Processor 256 is coupled with magnetic current generator 260, with optical detection assembly 264, with magnetic field receivers $266_1$ and $266_2$ and with display 268. System 250 aims to register the coordinate system associated with a model of object 258 with reference coordinate system 272. Object 258 includes at least three markers $270_1$ $270_2$ and $270_3$. At least one of markers $270_1$ $270_2$ and $270_3$ is a fiducial marker. In system 250, the position and orientation of reference unit 252 are fixed relative to object 258. For example, reference unit 252 is directly fixed to object 258. Alternatively, object 258 is fixed and reference unit 258 is also fixed. Thus, reference unit 252 is at fixed position and orientation relative to object 258 without being attached thereto. Alternatively, at least two additional magnetic field receivers (not shown) are attached to object 258. Thus, processor 256 can determine relative position and orientation between reference unit 252 and object 258.

Similar to as described above in conjunction with FIGS. 1A-1C and 2, a user (not shown) moves portable unit 254 through at least two registration positions. For each registration position processor 256 determines the position and orientation of portable unit 254 in reference coordinate system 272 according magnetic field transmitted by transmitting elements $262_1$, $262_2$ and $262_3$ and received by magnetic field receivers $266_1$ and $266_2$. For each registration position, optical detection assembly 264 acquires an image of the fiducial ones of markers $270_1$ $270_2$ and $270_3$. For each registration position processor 256 determines a respective direction toward each of the fiducial ones of markers $270_1$ $270_2$ and $270_3$, relative to optical detection assembly 264, according to the image acquired by optical detection assembly 264. Each direction defines a line in reference coordinate system 272 and the intersection of the three lines, associated with each marker, defines the location of that marker in reference coordinate system. A user may also employ a tracked pointer (not shown) to determine the location of markers $270_1$ $270_2$ and $270_3$. Since the coordinates of the markers $270_1$ $270_2$ and $270_3$ in the coordinate system associated with the model are known, system 250 can determine the correspondence between the location of markers $270_1$ $270_2$ and $270_3$ in the referenced coordinate system 272 and the location of the markers in the model coordinate system. Thus, registration between the model coordinate system and reference coordinate system 272 is achieved. When processor 256 determines at least an initial registration between the coordinate system associated with the model of object 258 with reference coordinate system 272, processor 256 may display on display 268 registration related information as further explained below.

Figure 4:
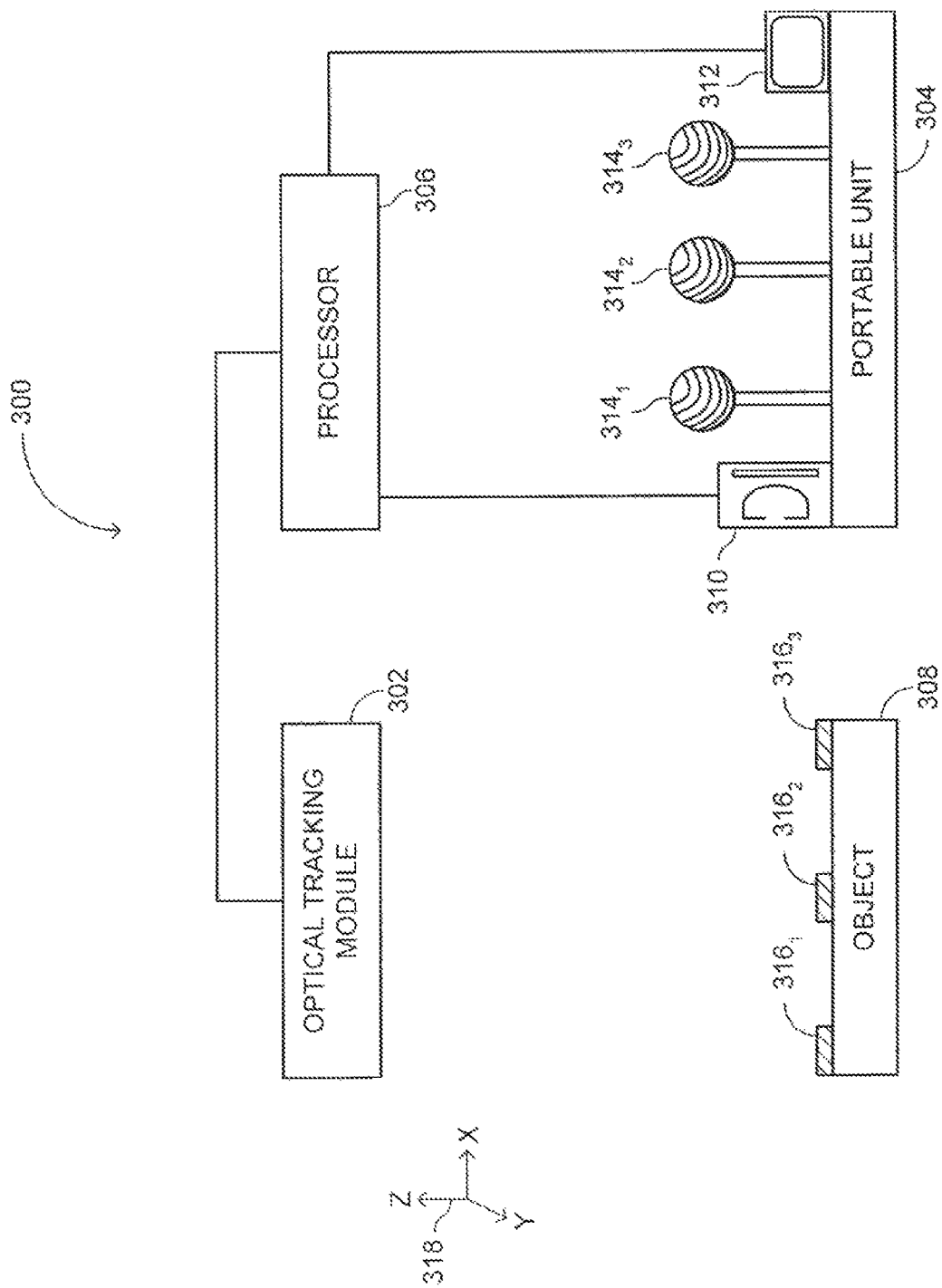
FIG. 4 is a schematic illustration of an optical tracking system which tracks the location of the portable unit in a reference coordinate system, constructed and operative in accordance with another embodiment of the disclosed technique.

Reference is now made to FIG. 4, which is a schematic illustration of an optical tracking system, generally referenced 300, which tracks the location of the portable unit in a reference coordinate system, constructed and operative in accordance with another embodiment of the disclosed technique. System 300 includes an optical tracking module 302, a portable unit 304 and a processor 306 which exhibits the out-in configuration. Portable unit 304 includes an optical detection assembly 310 and at least three light emitters $314_1$ $314_2$ and 314. Portable unit 304 also includes a display 312. In FIG. 4, light emitters $314_1$ $314_2$ and 314 take the form of reflective spheres which reflect light impinging thereon. Optical detection assembly 310 is for example sensor array camera, a PSD, a stereoscopic camera or a TOF camera.

Processor 306 is coupled with optical tracking module 302, with optical detection assembly 310 and with display 312. System 300 aims to register the coordinate system associated with a model of object 308 with reference coordinate system 318. Object 308 includes at least three markers $316_1$ $316_2$ and $316_3$. At least one of markers $316_1$ $316_2$ and $316_3$ is a fiducial marker. In system 300, the position and orientation of reference unit optical tracking module 302 are fixed relative to object 308.

Optical tracking module 302 may be embodied as stereoscopic camera (i.e., two cameras, directed toward substantially the same Field Of View and exhibiting a fixed and known relative position and orientation between the two cameras). Alternatively, optical tracking module 302 may be embodied as a Time-Of-Flight (TOF) camera which includes a light emitter which emits modulated light (e.g. continuous wave modulated light or pulsed modulated light) and an optical detector. When optical tracking module 302 is embodied as a stereoscopic camera, processor 306 determines the location of each one of light emitters $314_1$ $314_2$ and $314_3$ using triangulation. Thus, processor 306 can determine the position and orientation of portable unit 304 in reference coordinate system 318. When optical tracking module 302 is embodied as a TOF camera, each image includes the depth information of each pixel (i.e., the distance between the TOF camera and the object being imaged) and each pixel provides the direction from the TOF camera toward the object being imaged. Thus, an image of light emitters $314_1$ $314_2$ and $314_3$ includes information relating to the location of these light emitters in reference coordinate system 318. Thus, processor 306 can determine the position and orientation of portable unit 304 in reference coordinate system 318.

Similar to as described above in conjunction with FIGS. 1A-1C and 2, a user (not shown) moves portable unit 304 through at least two registration positions. For each registration position processor 306 determines the position and orientation of portable unit 304 in reference coordinate system 318 according to the images acquire by optical tracking module 302. For each registration position, optical detector 304 acquires an image of the fiducial ones of markers $316_1$ $316_2$ and $316_3$. For each registration position, processor 306 determines a respective direction toward the fiducial ones of markers $316_1$ $316_2$ and $316_3$, relative to optical detection assembly 310, according to the image acquired by optical detection assembly 310. Each direction defines a line in reference coordinate system 318 and the intersection of the two lines, associated with each marker, defines the location of that marker in reference coordinate system. The user may alternatively employ a tracked pointer to determined location of markers $316_1$ $316_2$ and $316_3$. Since the coordinates of the markers $316_1$ $316_2$ and $316_3$ in the coordinate system associated with the model are known, system 30 can determine the correspondence between the location of markers $316_1$ $316_2$ and $316_3$ in the referenced coordinate system 318 and the location of the markers in the model coordinate system. Thus, registration between the model coordinate system and reference coordinate system 318 is achieved. When processor 306 determines at least an initial registration between the coordinate system associated with the model of object 308 with reference coordinate system 318, processor 306 may display on display 268 registration related information as further explained below.

Reference is now made to FIG. 5, which is a schematic illustration of an optical tracking system, generally referenced 350, which tracks the location of the portable unit in a reference coordinate system, constructed and operative in accordance with a further embodiment of the disclosed technique. System 350 includes a portable unit 352, a reference unit 354 and a processor 356. Portable unit 352 includes an optical tracking module 362 coupled with processor 356. Portable unit 352 further includes a display also coupled with processor 356. Reference unit 354 includes at least three light emitters $360_1$ $360_2$ and $360_3$ and is attached to object 358. In the example brought forth in FIG. 5, light emitters $360_1$ $360_2$ and $360_3$ are LEDs. Object 358 includes three markers $366_1$ $366_2$ and $366_3$, one of which is a fiducial. Also, the relative position between reference unit 354 and object 358 is fixed.

Similar to optical tracking module 302 (FIG. 4), optical tracking module 362 may be embodied as a stereoscopic camera or a TOF camera. When the optical tracking module includes a stereoscopic camera or a TOF camera, a single registration position is sufficient to determine the location of markers $366_1$, $366_2$ and $366_3$ in reference coordinate system 368 (i.e., assuming all of the fiducial one of markers $366_1$ $366_2$ and $366_3$ are within the Field Of View of optical tracking module 362).

Accordingly, optical tracking module 362 acquires an image or images of light emitters $360_1$ $360_2$ and $360_3$ and processor 356 determines the location optical tracking unit 362 and consequently of portable unit 352 in reference coordinate system 368. Also, optical tracking module 362 acquires an image or images of the fiducial one of markers $366_1$ $366_2$ and $366_3$, and processor 356 determines the location of markers $366_1$ $366_2$ and $366_3$ relative to optical tracking module 362. Since processor 356 determined the location of optical tracking unit 362 in reference coordinate system 368, processor 356 can determine the location of the fiducial ones of markers $366_1$ $366_2$ and $366_3$ in reference coordinate system 368. The user may alternatively employ a tracked pointer (e.g., tracked in a coordinate system associated with portable unit 352) to determined location of markers $366_1$ $366_2$ and $366_3$. Since the coordinates of the markers $366_1$ $366_2$ and $366_3$ in the coordinate system associated with the model are known, system 360 can determine the correspondence between the location of markers $366_1$ $366_2$ and $366_3$ in the referenced coordinate system 368 and the location of the markers in the model coordinate system. Thus, registration between the model coordinate system and reference coordinate system 368 is achieved. When processor 356 determines at least an initial registration between the coordinate system associated with the model of object 358 with reference coordinate system 368, processor 356 may display on display 268 registration related information as further explained below.

In the examples brought herein above in conjunction with FIGS. 1A-1C, 2, and 5, the optical detection assembly located on the portable unit is employed for both tracking the portable unit and for registration. However, the portable unit may include two separate optical detection assemblies, one employed for tracking the portable unit and the other employed for registration.

With respect to any of the tracking systems described hereinabove in conjunction with FIGS. 1A-1C, 2, 3, 4 and 5, during the registration process, information relating to the registration process may be displayed to the user (i.e., on the respective display associated with any one of the tracking system described hereinabove in conjunction with FIGS. 1A-1C, 2, 3, 4 and 5). This registration related information may be, for example, a marker identifier (e.g., a number, a character), an indication that a marker has been identified, an indication that a marker has been located, the error associated with the determined location of the marker, a score indicating the quality of the registration (e.g., the estimated error of the registration), instructions to the user and the like.

For example, once the location of a marker is determined, a marker indicator may be displayed to the user, for example, by superimposing the indicator (e.g., a circle, a square, an arrow and the like) on the marker, thus providing the user with information regarding the progress of the registration process. Each kind of marker (i.e., either fiducial or anatomical landmark) may have a corresponding indicator (e.g., a circle for fiducials and a square for anatomical landmarks). When the positions of a sufficient number of markers are determined (i.e., at least three when registering three dimensional coordinate systems) and registration is calculated, a score indicating the quality of the registration may be displayed to the user. The registration related information may further include user related information such as user selection or user guidance. For example, the user may direct the tracking system whether the score is good enough or whether to continue the registration process (e.g., by enabling the system to locate additional markers). For example, when the markers are located on both sides of the head, then the system may direct the user to physically look at the head of the patient from the other side to allow the system to identify additional markers. To improve the accuracy of the registration, the system may further guide the user to look at the head of the patient from the other side, even if the registration was already successful using markers from only one side of the head of the patient. Once an initial registration is determined (e.g., may be with a large error), the system may also direct the user (e.g., via the display) to markers that location thereof has yet to be determined or that the location thereof was determined with a large error. The system may also indicate to the user the error that each marker contributed to the final calculation of the registration. The user may also discard the use of specific markers in the calculation of the registration. Discarded markers may be indicated with a different indicator than the markers that were employed for registration (e.g., discarded markers shall be marked with a red square). For example if the user suspects that certain markers may have moved since the preoperative image has been acquired. Also, the surgeon may request that the registration be recalculated without using certain markers.

Reference is now made to FIGS. 6A, 6B, 6C and 6D, which are schematic illustrations of an exemplary registration process where registration related information is displayed to the user, for example on a visor 400, during the registration process, in accordance with another embodiment of the disclosed technique. The user observes patient 402 lying on treatment bed 404. In the example set forth in FIGS. 6A-6D, a reference unit 406 is at a fixed position and orientation relative to the head of patient 402. Reference unit 406 may be any one of the reference units described above in conjunction with FIGS. 1A-1C, 2, 3, 4 and 5. In the example brought forth in FIGS. 6A-6D, reference unit 406 includes three LEDs $408_1$, $408_2$ and $408_3$. Alternatively, reference unit may include magnetic field transmitters or receivers as explained above. Furthermore, marker $401_1$, $410_2$, $410_3$, $410_4$, $410_5$, $410_6$ and $410_7$ are located on patient 402 (i.e., either fiducials or anatomical landmarks or both).

Figure 6A:
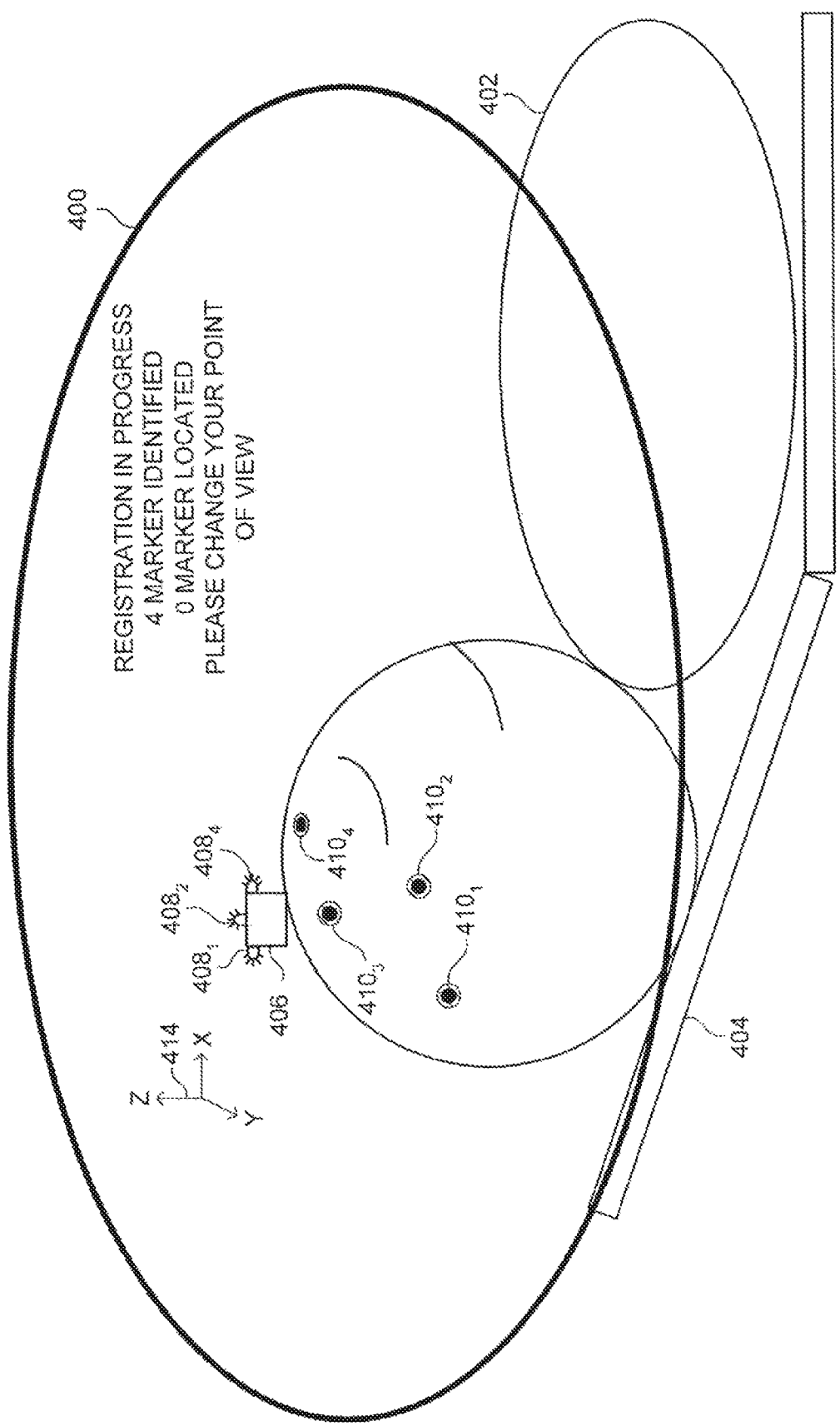
FIGS. 6A, 6B, 6C and 6D are schematic illustrations of an exemplary registration process where registration related information is displayed to the user, during the registration process, in accordance with another embodiment of the disclosed technique.

With reference to FIG. 6A, the user is located at a first registration position. At this first registration position, the user views markers $410_1$, $410_2$, $410_3$ and $410_4$. A registration system according to the disclosed technique identifies markers $410_1$, $410_2$ $410_3$ and $410_4$ (e.g., markers $410_1$, $410_2$, $410_3$ and $410_4$ are within the field of view of an optical detector) and informs the user (e.g., by displaying text on visor 400) that four markers have been identified. Furthermore, the system (e.g., any of the systems described hereinabove) instructs the user to change the point of view thereof. It is noted that when a stereoscopic camera or a TOF camera are employed with the portable unit, the system is also able to determine the location of markers $410_1$, $410_2$ $410_3$ and $410_3$ from a single registration position.

Figure 6B:
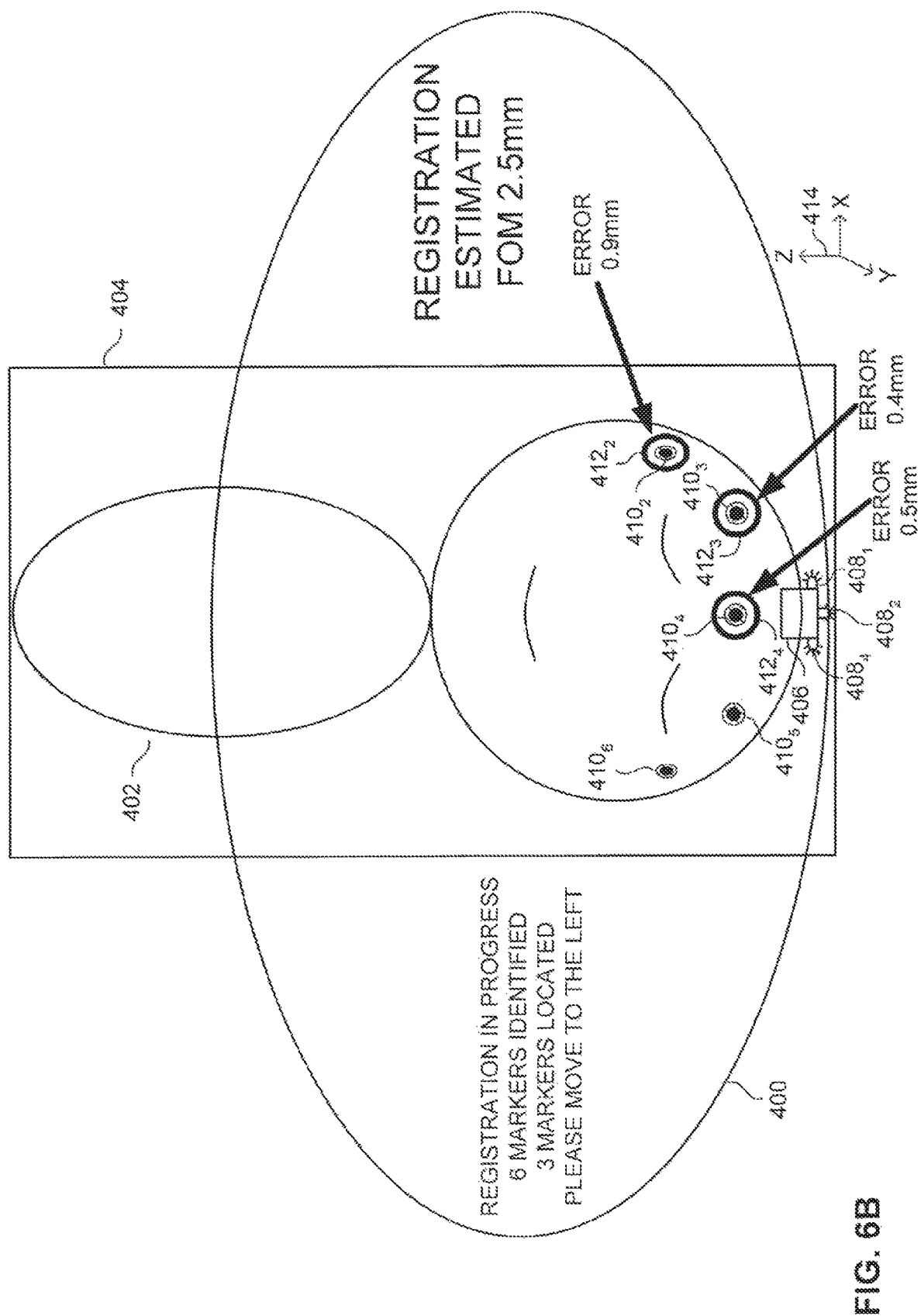
Figure 6C:
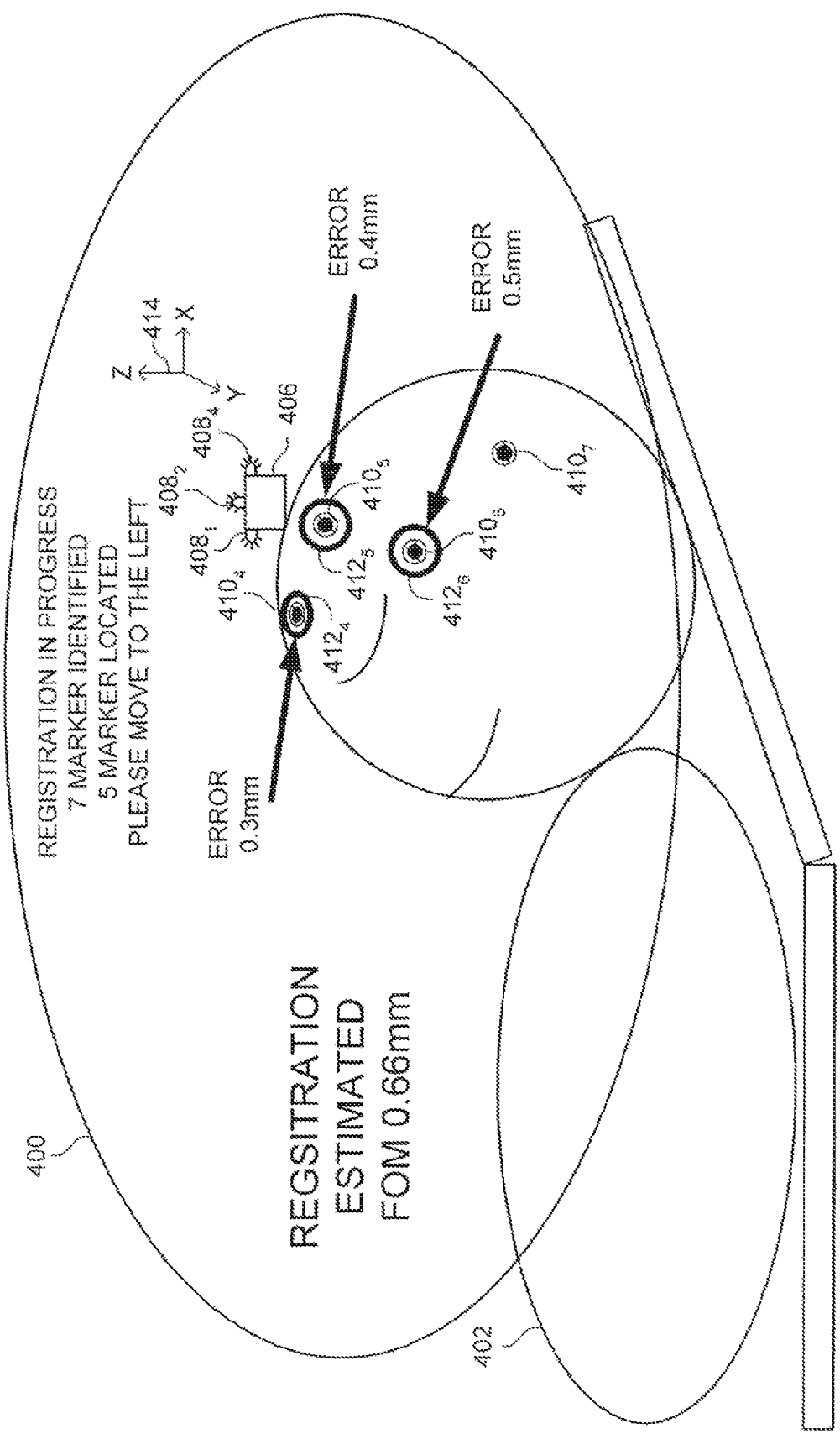
Figure 6D:
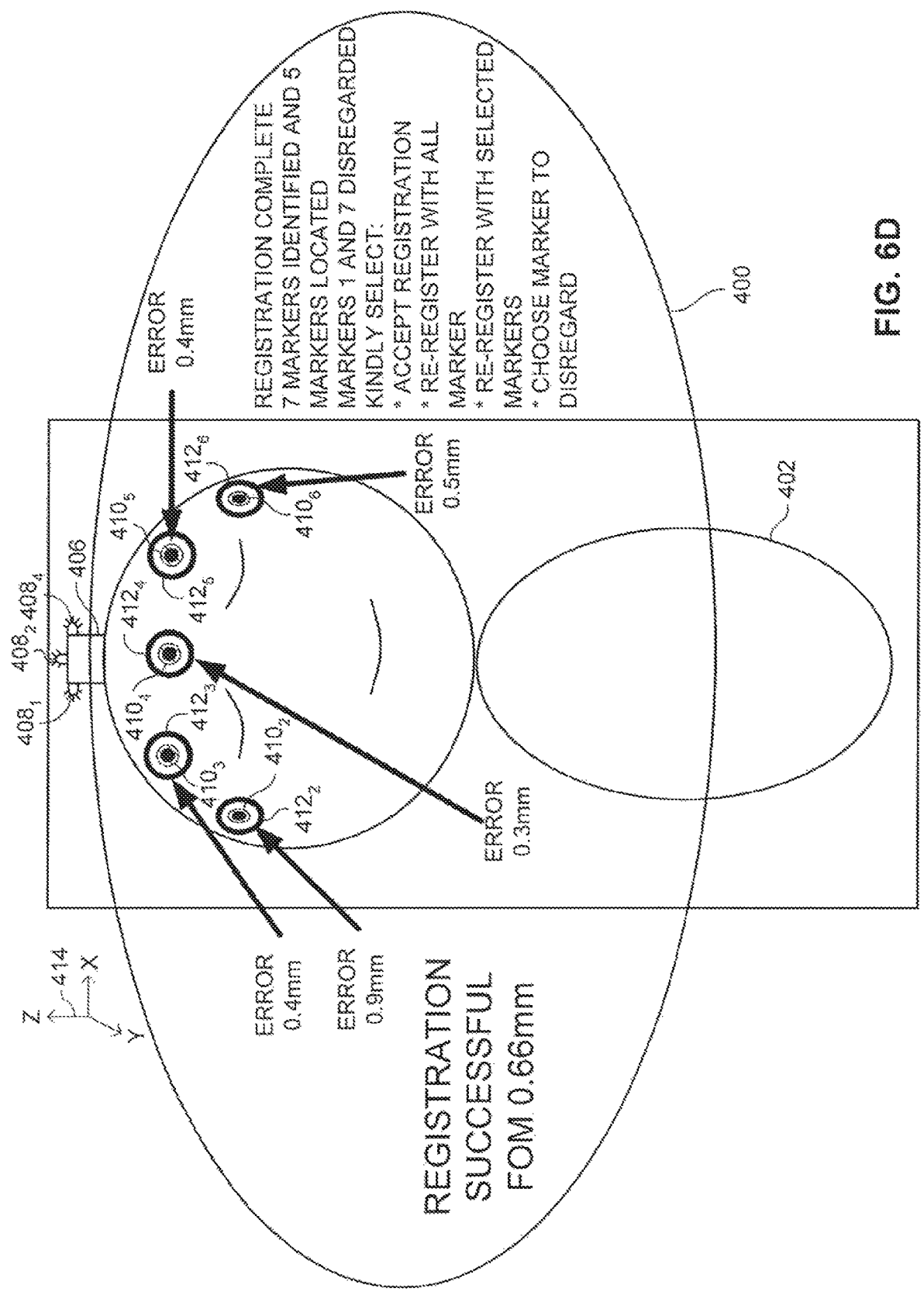

With reference to FIG. 6B, the user is located at a second registration position. At this second registration position, the user views markers $410_2$, $410_3$, $410_4$, $410_5$ and $410_6$. The registration system according to the disclosed technique further identifies markers $410_5$ and $410_6$ (e.g., markers $410_2$, $410_3$, $410_4$, $410_5$ and $410_6$ are within the field of view of an optical detector) and informs the user that 6 markers have been identified. Furthermore, the registration system determines the location of markers $410_2$, $410_3$ and $410_4$ and displays respective marker indicators $412_2$, $412_3$ and $412_4$ on display 400, superimposed over the respective marker thereof, as seen by the user through the transparent visor. Since the system according to the disclosed technique tracks a portable unit in the reference coordinate system, the system can determine the P&O of the display. Since the system also determines the location of the markers, the system can superimpose a marker indicator at the display location which is related to the position of the markers as seen on or through the display. In general, the registration system displays the registration related information at a display location which corresponds to the position and orientation of the portable unit. The registration system may display the registration related information at a display location which is related to the position of the markers. In FIGS. 6B-6D, marker indicator $412_2$, $412_3$ and $412_4$ take the form of circles. The registration system also provides the user with an indication of the error of the determined location thereof. For example, the registration system determined the position of marker $410_2$ with an error of 0.9 mm, marker $410_3$ with an error of 0.3 mm and marker $410_4$ is located with an error of 0.5 mm. It is noted that the size, color or shape of the marker indicator may be related to the error associated with the position of that marker. For example, the diameter of the circle is proportional to the location of the marker over which that circle is superimposed. Since three markers have been identified, the system can estimate the registration between the reference coordinate system and the coordinate system associated with the model of the patient. However, this registration may be an initial registration with a relatively large error (e.g., 2.5 millimeters in the example set forth in FIG. 6B). Nevertheless, since the spatial relationship (i.e., the relative position) between the markers is known, the system can instructs the user to move toward markers which are yet to be detected (i.e., in general, the registration related information includes instructions to the user). In FIG. 6B, the system informs the user that 6 markers have been identified and 3 located. Furthermore, the system displays on display 400 instructions to the user to move to the left.

With reference to FIG. 6C, the user is located at a third registration position. At this third registration position, the user views markers $410_4$, $410_5$ $410_6$ and $414_7$. The registration system according to the disclosed technique further identifies marker $410_7$ (e.g., markers $410_4$, $410_5$, $410_6$ and $410_7$ are within the field of view of an optical detector). The registration system according to the disclosed technique determines the location of markers $410_5$ and marker $410_6$ and marks these markers with a respective circle $412_5$ and $412_6$. The system determined the position of marker $410_5$ with an error of 0.4 mm, marker $410_6$ with an error of 0.5 mm. Furthermore, the system improved the location estimation of marker $410_4$ and the location error associated with marker $410_4$ is now 0.3 mm. The system was not able to determine the location of markers $414_7$ as well as of marker $410_1$. The system also improved the registration error (e.g., 0.66 millimeters in the example set forth in FIG. 6C). The system further instructs the user to move to the left.

With reference to FIG. 6D, the registration system according to the disclosed technique displays on display 400 a summary of the registration process for the user and indicates that the registration is complete and the displays the registration error (i.e., the registration related information includes, for example, a summary of the registration process for the user and indicates that the registration is complete and displays the registration error). The system further displays information relating to the markers employed for registration and various options for the user to choose from. In general, as explained above, the system displays registration related information to a user at a display location related to the position and orientation of the portable unit. It is noted that since the system determines the position of the markers, the system may adjust the information displayed on the display accordingly. For example, the marker indicators may be displayed at a display location corresponding to the position of the markers as seen on or through the display, while the registration error, instructions to the user and the like may be displayed at a different selected location which does not interfere with the marker indicators.

Figure 7:
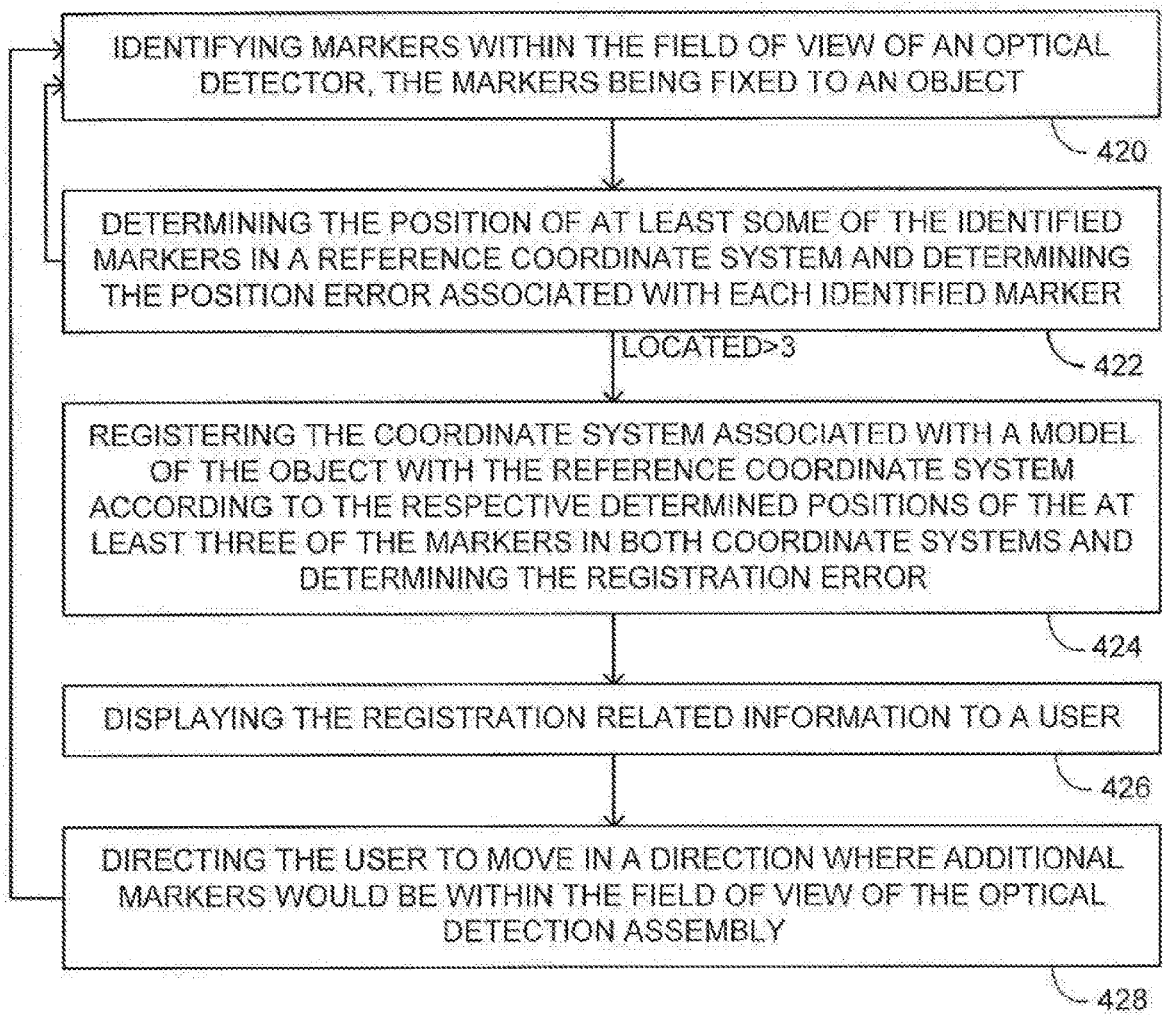
FIG. 7 is a schematic illustration of a method for displaying registration related information to a user, in accordance with a further embodiment of the disclosed technique.

Reference is now made to FIG. 7, which is a schematic illustration of a method for displaying registration related information to a user, in accordance with a further embodiment of the disclosed technique. In procedure 420, markers within the field of view of an optical detector are identified. The markers are fixed to an object. These markers may be fiducial markers or anatomical landmarks. With reference to FIGS. 6A-6D, markers $410_1$, $410_2$, $410_3$, $410_4$, $410_5$, $410_6$ and $410_7$, which are within the field of view of an optical detector are identified.

In procedure 422, the positions of at least some of the identified markers, in a reference coordinate system, are determined. Furthermore, the position error of the identified markers is also determined. With reference to FIGS. 6A-6D, a processor (not shown) determines the position of at least some of markers $410_1$, $410_2$, $410_3$, $410_4$, $410_5$, $410_6$ and $410_7$ in reference coordinate system 414. When the positions of at least three markers are identified, the method proceeds to procedure 424. Otherwise, the method returns to procedure 420.

In procedure 424, the coordinate system associated with a model of the object is registered with the reference coordinate system, according to the respective positions of the at least three of the identified markers in both coordinate systems. Furthermore, the registration error is determined. With reference to FIGS. 6A-6D a processor registers reference coordinate system 414 with the coordinate system associated with a model of patient.

In procedure 426, registration related information is determined and displayed to the user. As mentioned above, registration related information may further include user related information such as user selection or user guidance. With reference to FIGS. 6A-6D, registration related information is displayed on visor 400.

In procedure 428, the user is directed to move in a direction where additional markers would be within the field of view of the optical detection assembly. Since at least initial registration is determined, the location of all markers in the reference coordinate system can be estimated. Thus, the location of these markers relative to the location of the portable unit can also be determined. It is noted that directing the user in a direction where additional markers would be within the field of view of the optical detection assembly is optional and may occur when the registration process is yet to be completed (e.g., when the registration error is above a threshold or the user selects to continue the registration process). With reference to FIG. 6B, the user is directed to move to the right in order to identify and located additional markers. After procedure 428 the method returns to procedure 420.

In general, there are three types of error estimations involved in the registration process. The first is the error estimation (herein 'type one error estimation') relates to the error of the position of a single marker in the reference coordinate system. This error results from the residual error of the triangulation process (i.e., lines intersection), the angular difference between the lines and the location error of the portable unit. This error may be relatively large when the marker was partially obscured from some direction, smudged by blood and the like, or when the angular difference between the directions associated with the marker is relatively small. In such a case the user may be instructed to move to another registration position so the marker may be sampled from an additional direction. The error may also be large if the user moved relatively fast while the marker was sampled (i.e., when the direction from the portable unit toward the marker was determined). Such an error may be detected automatically and the user may be instructed, for example, to move slower. The second type of error estimation for each marker (herein 'type two error estimation') relates to the distance between the position of the markers in the registered model coordinate system (i.e. the image coordinate system after the rotation and translation onto the tracker coordinate system according to the calculated registration) and the position of the marker in the reference coordinate system. A specific marker may have been displaced between the time the imaging was performed and the time the registration is performed, but still be accurately located. In such a case, this marker will exhibit a small estimated error of the first type and a large estimated error of the second type and the system may discard it automatically or recommend to the user to discard it manually. Consequently, the registration may be improved. The third type of error estimation (herein 'type three error estimation') is the figure of merit of the registration calculation, which may be the average of the errors of the second type for all the markers, or any other objective function (i.e., the objective of the registration calculation is to minimize this error). All of the above types of error estimations may be calculated and displayed to the user (e.g., in millimeters).

Reference is now made to FIG. 8, which is a schematic illustration of a method for registering a model coordinate system and a reference coordinate system in accordance with another embodiment of the disclosed technique. In procedure 450, the position of each of the at least three markers is determined in a coordinate system associated with a model of an object. At least one of the at least three markers is a fiducial marker. When the model is, for example, an image, the location of the markers may be determined by employing image processing techniques. Alternatively, the location of markers may be manually marked on a screen. After procedure 450, the method proceeds to procedure 460.

In procedure 452 the position of at least one anatomical landmark is determined in the reference coordinate system, when at least one anatomical landmark is employed as a marker. With reference to FIG. 2, when the at least part of the markers are anatomical landmarks, physician 224 employs a pointer. In such a case medical tool 222 takes the form of a pointer. Physician 224 places the tip of the pointer on the anatomical landmark. Processor 214 determines the location of the pointer (i.e., of medical tool 222), and thus of the marker, in reference coordinate system 230 as described above. After procedure 452, the method proceeds to procedure 460.

In procedure 454, for each of at least one registration position, the position and orientation of a portable unit in a reference coordinate system is determined. The portable unit includes an optical detection assembly. When the optical detection assembly is an optical detector (e.g., a sensor array camera or a PSD) then, the number of registration positions is at least two. When the optical detection assembly is a stereoscopic camera or a TOF camera, the number of registration positions is at least one. With reference to FIGS. 1A-1C, a user 106 moves moving optical detector 102 (i.e., which, as mentioned above, defined the portable unit together with light emitters $104_1$ and $104_2$) through at least two registration positions. Moving optical detector 102 acquires at least one image of light emitter 110 and moving optical detector acquires at least one image of light emitters $104_1$ and $104_2$. A Processor (e.g., processor 214—FIG. 2) determines the position and orientation of the relative position between reference optical detector and a moving optical detector is determined in reference coordinate system 116 according to the representations of light emitters $104_1$, $104_2$, and 110. With reference to 5, optical tracking module 362 may be embodied as either a TOF camera or a stereoscopic camera which acquires which acquires an image or images of light emitters $360_1$ $360_2$ and $360_3$. Processor 356 determines the location of optical tracking unit 362, and consequently of portable unit 352, in reference coordinate system 368.

In procedure 456, for each of the at least one registration position, location related information respective of each of the at least one fiducial that are within the field of view of the optical detection assembly, is determined. When the portable unit includes an optical detector (e.g., a sensor array camera or a PSD), the position related information includes a respective directions toward each of the at least one fiducial marker located on the object. When the portable unit includes, for example, a stereoscopic camera or a TOF camera, the position related information may be related directly to the position of the fiducial in the reference coordinate system (e.g., two directions from the two detectors in the stereoscopic camera or pixel depth information from the TOF camera). With reference to FIGS. 1A-1C, when moving optical detector 102 acquires the image or images of light emitter 110, moving optical detector 102 also acquires and image of markers $114_1$, $114_2$, $114_3$ and $114_4$. For each registration position, the processor determines position related information of markers $114_1$, $114_2$, $114_3$ and $114_4$, relative to moving optical detector 102, according to the image of markers $114_1$, $114_2$, $114_3$ and $114_4$. With reference to FIG. 5, optical racking module 362 With reference to 5, optical tracking module 362 may be embodied as either a TOF camera or a stereoscopic camera, which acquires an image or images of markers $366_1$ $366_2$ and $366_3$. Processor 356 determines the location of markers $366_1$ $366_2$ and $366_3$ determines the location of the fiducial ones of markers $366_1$ $366_2$ and $366_3$ in reference coordinate system 368.

In Procedure 458, the position of each of the at least one fiducial marker located on the object is determined in the reference coordinate system, according to the positions and orientations of the portable unit in each of at least two registration positions and the respective position related information of each of the at least one fiducial marker. For example each direction defines a line in the reference coordinate system. The intersection of the at least two directions associated with each fiducial defines the location of that fiducial in the reference coordinate system. As mentioned above, in practice these lines may not intersect. In such a case, the point exhibiting the minimum distance to each of the lies is determined as the location of the marker. With Reference to FIGS. 1A-1C and 2, a processor (e.g., processor 214—FIG. 2), determines the position of each of the at least three markers (e.g., markers $114_1$, $114_2$, $114_3$ and $114_4$ in FIG. 2 or $232_1$, $232_2$, $233_3$ in FIG. 2) in reference coordinate system (e.g., referenced coordinate system 116 in FIG. 1 or reference coordinate system 230 in FIG. 2).

In procedure 460, the coordinate system associated with the model of the object is registered with the reference coordinate system, according to the respective positions of at least three of the at least three markers, in both coordinate systems. With Reference to 2, processor 214 registers the coordinate system associated with the model of the object with reference coordinate system 230, according to the respective positions of the markers in both coordinate systems.

The description herein above relates to an automatic registration process with an augmented reality environment, where the registration system displays registration related information overlaid on the display, at a display location which corresponds to the position and orientation of the portable unit and the location of the markers in a reference coordinate system. In general, each one of the displays described above may be hand held or head mounted) or part of any portable unit in general (e.g. attached to a moveable arm). For example, a video see-through portable unit includes a tablet computer and a camera. A video see-through portable unit may alternatively include an HMD with a non-transparent near-eye display and a video camera. In a video see-through portable unit the video from the camera is augmented and displayed to the user in the display. When an optical tracking system is employed for tracking a video see-through portable unit, the camera employed for tracking and for the video see-through may be one and the same. An optical see-through portable unit includes, for example, a tablet computer with a transparent display, or a projector and a half-silvered mirror attached to a movable arm. An optical see-through portable unit may alternatively include an HMD with a visor-projected display or a transparent near-eye display.

The descriptions herein above exemplified the registration process with the user moving through at least two different registration positions. However, in practice, when the location of the markers is determined with the aid of the portable unit, the user may move the portable unit without constraints around the patient, while maintaining the patient within the FOV of the optical detector of the portable unit. The optical detector detects the markers during the motion of the portable unit (e.g., acquires an image when an imaging sensor is employed). The tracking system determines the position and orientation of the potable unit each time a marker is detected and determines the location of the markers as described above, both at a relatively high frequency (e.g., on the order tens of times per second).

Figure 9A:
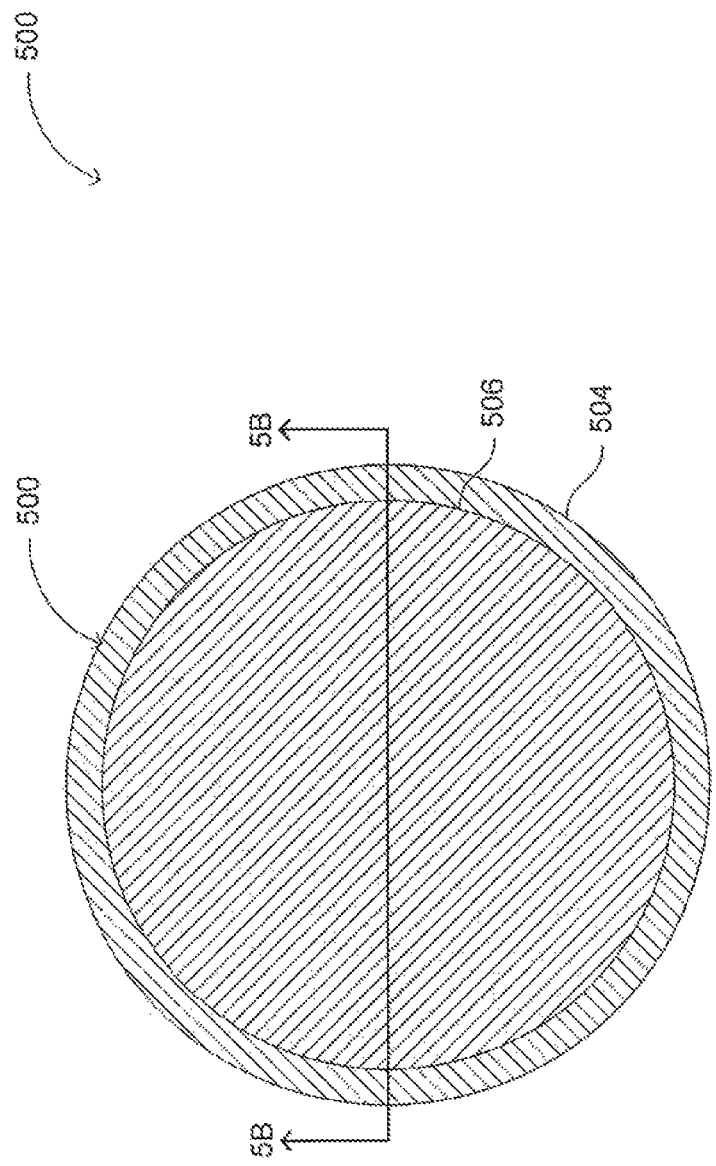
FIGS. 9A and 9B are schematic illustrations of an exemplary standard marker.
Figure 9B:
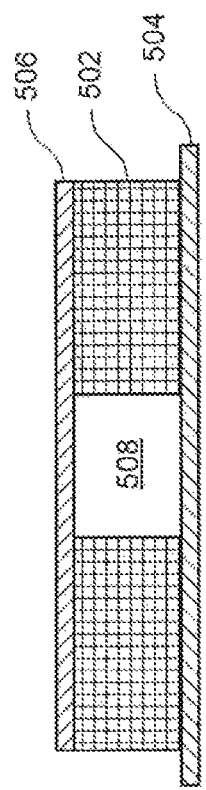
Figure 9C:
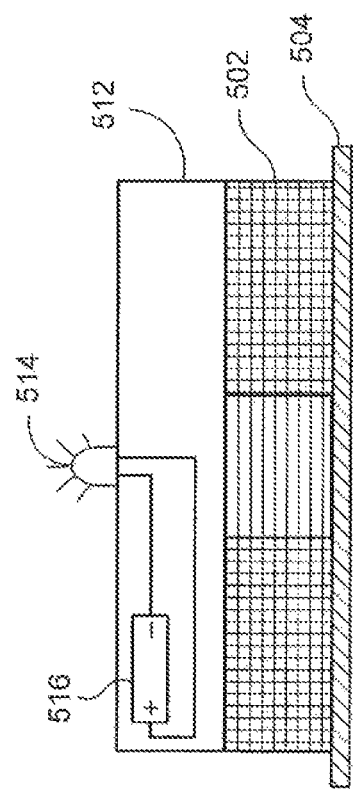
FIGS. 9C-9E are schematic illustrations of an exemplary active registration marker, constructed and operative in accordance with a further embodiment of the disclosed technique.
Figure 9D:
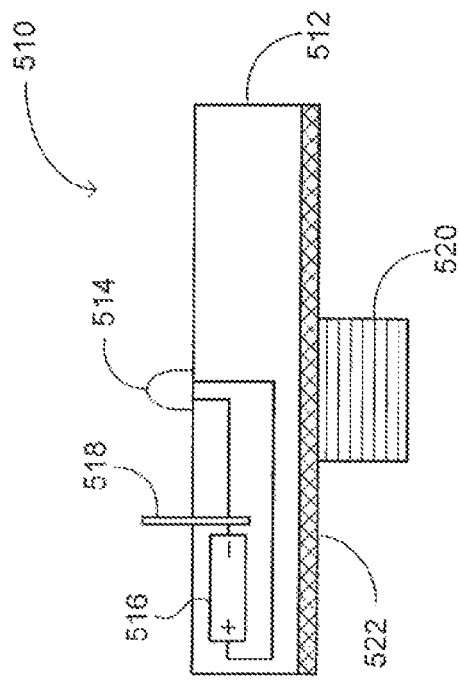
Figure 9E:
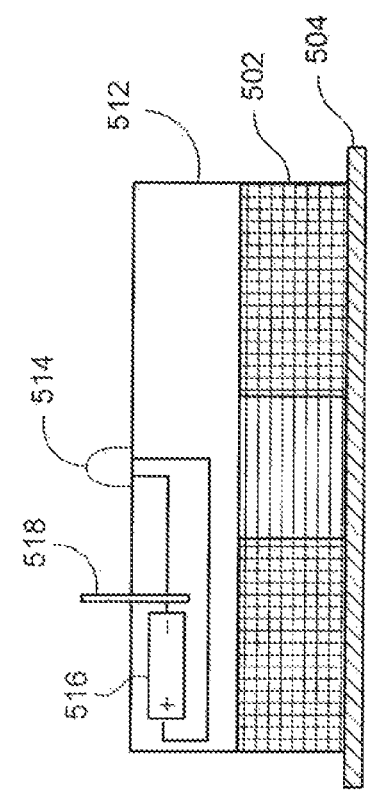

Reference is now made to FIGS. 9A-9E. FIGS. 9A and 9B are schematic illustrations of an exemplary standard marker, generally referenced 500. A standard marker 500 is employed during model acquisition (e.g., during CT or MRI imaging). FIGS. 9C-9E are schematic illustrations of an exemplary active registration marker, generally reference 510, constructed and operative in accordance with a further embodiment of the disclosed technique, which may be attached to a standard marker 500. Active registration marker 510 is employed during registration. FIG. 9A is a top view of a standard marker 500 and FIG. 9B is a cross section view of a standard marker 500. In the example brought forth herein, the standard marker 500 is in the form of a ring which forms a cavity 508. Standard marker 500 includes a marker body 502, and a bottom sticker 504. Bottom sticker 504 is employed for attaching marker 350 to the patient. Marker body 502 is made of a material which may be detected in the acquired model (e.g., a radio-opaque material for CT imaging). Marker 500 may also have a cover 506 that protects the marker from damage and is removed before the registration process.

As mentioned above, the markers described hereinabove in conjunction with FIGS. 1A-1C 2, 3, 4, 5 and 6A-6D, may be passive markers or active markers. A passive marker reflects the light impinging thereon. An active marker includes a LED and a battery and is activated just before initiation of the registration process starts. With reference to FIG. 9C, active registration marker 510 includes a housing 512, an LED 514, a power supply 516, a detachable isolator 518, a protrusion 520 and a sticker 522. LED 514 is coupled with power supply 516. Detachable isolator 518 isolates LED 514 from power supply 516. In general, power supply 516 takes the form of a battery. However, power supply 516 may also take to form of a preloaded capacitor. With reference to FIG. 9D, before active registration marker 510 is attached to standard marker 500, sticker 522 is removed exposing an adhesive. Thereafter, protrusion 520 is inserted into cavity 508 and housing 512 is fixedly attached to marker body 502. With reference to FIG. 9E, once active registration marker 510 is attached to marker body 502, detachable isolator 518 is removed thereby connecting LED 514 to power supply 516. Thus, LED 514 starts to emit light.

As mentioned above, the registration marker may also be a passive registration marker. Such a passive registration marker may be a reflector or a retro-reflector. Reference is now made to FIG. 10, which is a schematic illustration of cross-sectional view of a passive registration marker, generally referenced 550, constructed and operative in accordance with another embodiment of the disclosed technique. Passive registration marker 550 is exemplified herein as a corner cube retro-reflector. Passive registration marker includes a housing 552, a corner cube retro-reflector 554, a protrusion 558 and a sticker 560. Corner cube retro-reflector 554 includes three mirrors. Two mirrors $556_1$ and $556_2$, of the three mirrors included in a corner cube reflector 554 are depicted in FIG. 8. Light impinging on corner cube retro-reflector is reflected back toward the direction from which that light arrived. Similar to active registration marker 510 (FIGS. 7C-7E), passive registration marker may be fixedly attached to a standard marker such as marker 500 (FIGS. 5A-5B), after the model acquisition process and before the registration process.

In general, the passive registration marker 550 is illuminated with the LED located on the portable unit (e.g., LEDS $104_1$ and $104_2$ of FIG. 1 or LEDs $206_1$ and $206_2$ of FIG. 2). The optical detector located on the portable unit (e.g., optical detector 102 of FIG. 1 or optical detector 202 of FIG. 2) acquires an image of the light reflected from passive registration marker 550. Thus, when passive registration marker 550 is embodied as a retro-reflector, it is important that the light emitters of the portable unit be located sufficiently close to the optical detector such that the light that is retro-reflected from passive registration 550 could be detected by the optical detector.

Figure 11B:
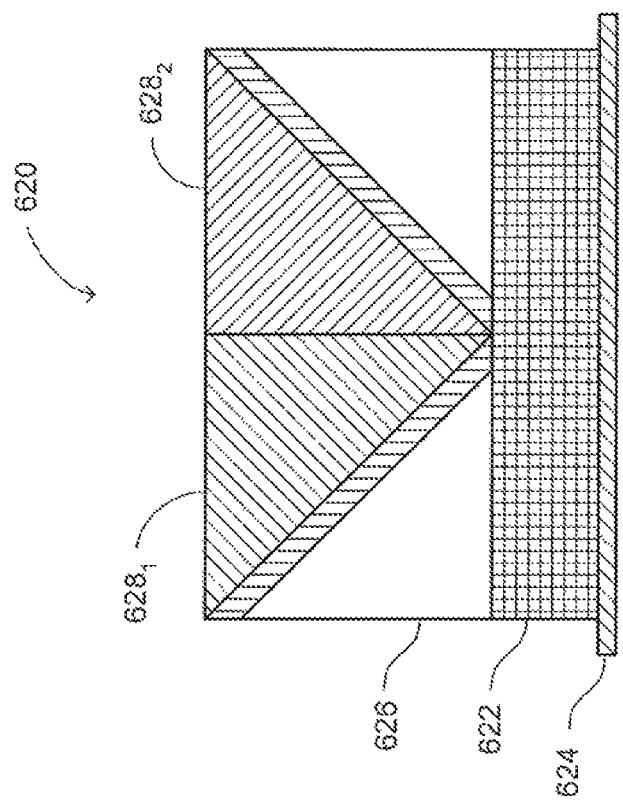
FIGS. 11A and 11B are schematic illustrations of two exemplary fiducial markers, which may be employed for both model acquisition and registration in accordance with a further embodiment of the disclosed technique.
Figure 11A:
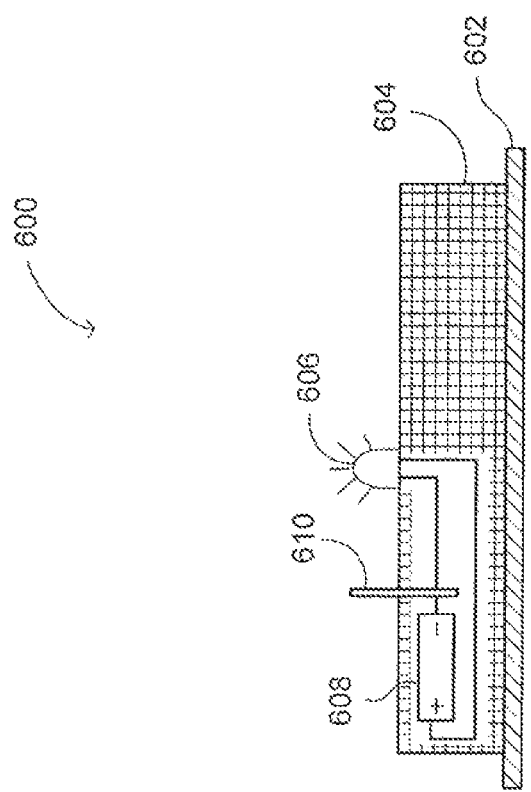

It is noted that the, according to the disclosed technique, a single fiducial marker may be employed during both model acquisition and registration. Reference is now made to FIGS. 11A and 11B, which are schematic illustrations of two exemplary fiducial markers, generally reference 600 and 620 respectively, which may be employed for both model acquisition and registration in accordance with a further embodiment of the disclosed technique. Fiducial marker 600 is an active fiducial marker and fiducial marker 620 is a passive fiducial marker.

With reference to FIG. 11A, fiducial marker 600 includes a body 602 which is made of a material which may be detected in the acquired model (e.g., a radio-opaque material for CT imaging), a sticker 604, an LED 606 a power supply 608 (e.g., a battery or a capacitor) and a detachable isolator 610. LED 606 is coupled with power supply 608. Detachable isolator 610 isolates LED 606 from power supply 608. Bottom sticker 604 is employed for attaching marker 600 to the patient. Thereafter, the model of the patient is acquired. Prior to the registration process, detachable isolator 610 is removed thereby connecting LED 606 to power supply 608. Thus, LED 606 starts to emit light.

With reference to FIG. 11B, fiducial marker 620 includes a body 622 is made of a material which may be detected in the acquired model, a sticker 624 and corner cube retro-reflector 626. Corner cube retro-reflector 626 includes three mirrors. Two mirrors $628_1$ and $628_2$, of the three mirrors included in a corner cube reflector 626 are depicted in FIG. 7B. Bottom sticker 624 is employed for attaching marker 620 to the patient. Thereafter, the model of the patient is acquired.

It will be appreciated by persons skilled in the art that the disclosed technique is not limited to what has been particularly shown and described hereinabove. Rather the scope of the disclosed technique is defined only by the claims, which follow.

The invention claimed is:

1. A system for registering a coordinate system associated with a pre-acquired model of an object with a reference coordinate system, the system comprising:
   a portable unit including:
      a display; and
      an optical detection assembly for detecting at least one representation of each of at least one marker located on said object;
   a tracking system for tracking said portable unit in said reference coordinate system; and
   a processor, coupled with said portable unit and with said tracking system, said processor configured to determine the position and orientation of said portable unit in said reference coordinate system, said processor further configured to determine at least position related information from said at least one representation, said processor further configured to display registration related information on said display, at least one of said registration related information and the display location of said registration related information being related to the position and orientation of said portable unit in said reference coordinate system,
   wherein the position of said at least one marker in said coordinate system associated with said pre-acquired model is predetermined.

2. The system according to claim 1, wherein said registration related information includes at least one of:
   a marker indicator;

a marker identifier;
an error associated with the determined location of a marker;
a registration score;
instructions to said user; or
user selection options.

3. The system according to claim 2, where said user instructions include at least one of:
instruction to change view point; or
instruction to move in a specified direction.

4. The system according to claim 2, wherein at least one of: the size of said marker indicator, the shape of said marker indicator, or the color of said marker indicator is related to at least one of type one error estimation or type two error estimation associated with each marker.

5. The system according to claim 1, wherein when at least some of said markers are fiducial markers, said processor is further configured to identify at least one of said fiducial markers being within the field of view of said optical detection assembly, said optical detection assembly being attached to said portable unit,
wherein for each of at least one registration positions, said processor is further configured to determine respective position related information of each of said at least one marker being within the field of view of said optical detection assembly, and
wherein said processor is further configured to determine the position of each of said at least one marker in said reference coordinate system according to the respective position and orientation of said portable unit in each of said at least one registration position and said position related information respective of each of said at least one marker.

6. The system according to claim 5, wherein said position related information is at least one of:
a direction from said portable unit toward said marker;
at least two directions from said portable unit toward said marker; or
a direction and a distance from said portable unit toward said marker.

7. The system according to claim 5, wherein said processor is further configured to direct said user to move in a direction where additional markers would be within the field of view of said optical detection assembly.

8. The system according to claim 5, wherein at least three light emitters are attached to said object, and
wherein said processor is further configured to determine the position and orientation of said portable unit according to at least one representation of each of said at least three light emitters acquired by said optical detection assembly.

9. The system according to claim 5, wherein a second optical detection assembly is attached to said object,
wherein, at least one light emitter is located on said object and at least one light emitter is located on said portable unit,
wherein, the total number of said light emitters is at least three, and
wherein said processor is further configured to determine the position and orientation of said portable unit according to at least one representation of said at least one light emitter located on said object and acquired by said optical detection assembly and at least one representation of said at least one light emitter located on said portable unit and acquired by said second optical detection assembly.

10. The system according to claim 1, wherein said optical detection assembly is a three dimensional optical detection assembly.

11. The system according to claim 10, wherein said optical detection assembly is a stereoscopic camera, and
wherein said position related information is at least two directions from said portable unit toward said marker.

12. The system according to claim 10, wherein said optical detection assembly is a time-of-flight camera, and
wherein said position related information is a direction toward said marker and a distance between said portable unit and said marker.

13. The system according to claim 1, wherein, said optical detection assembly is one of: a sensor array camera or a position sensitive device, and
wherein said position related information is at least one direction from said portable unit toward said marker.

14. The system according to claim 1, wherein at least some of said markers are anatomical landmarks.

15. The system according to claim 14, wherein said processor is further configured to determine the position of at least some of said markers according to the position and orientation of a tracked pointer in response to determining that said pointer touches each of said anatomical landmarks.

16. The system according to claim 1, wherein said portable unit is one of a head mounted display, a unit attached to a movable arm, or a hand held unit.

17. The system according to claim 16, wherein said display is one of:
optical see through display; or
video see through display.

18. The system according to claim 1, wherein the optical detection assembly comprises a position sensitive device, and wherein the representation comprises a direction of an arrival of light incident.

19. The system according to claim 1, wherein the optical detection assembly comprises an imaging sensor, and wherein the representation comprises an image.

20. The system according to claim 19, wherein the optical detection assembly further comprises a position sensitive device, and wherein the representation further comprises a direction of an arrival of light incident.

21. A method for displaying registration related information, the method comprising:
determining the position of markers in a coordinate system associated with a pre-acquired model of an object, said markers being located on said object;
determining the position and orientation of a portable unit in a reference coordinate system, said portable unit including a display and an optical detection assembly for acquiring at least one representation of each of said markers;
determining the position of at least three of said markers in a reference coordinate system from said at least one representation and said position and orientation of said portable unit;
registering said coordinate system associated with said pre-acquired model of the object with said reference coordinate system according to the respective determined positions of said at least three of said markers, in both coordinate systems; and
displaying registration related information on said display, at least one of said registration related information and the display location of said registration related information being related to the position and orientation of said portable unit in said reference coordinate system, wherein the method is performed by at least one processor.

22. The method according to claim 21, wherein said registration related information includes at least one of:
a marker indicator;
a marker identifier;
an error estimation associated with the determined location of a marker;
a registration error estimation;
instructions to a user; or
user selection options.

23. The method according to claim 22, where said user instructions include at least one of:
instruction to change view point; or
instruction to move in a specified direction.

24. The method according to claim 22, wherein at least one of the size of said marker indicator, the shape of said marker indicator, or the color of said marker indicator is related to at least one of type one error estimation or type two error estimation associated with each marker.

25. The method according to claim 21, where said determining the position of at least three of said markers further includes determining the position error estimation associated with each located marker, and
wherein said registering further includes determining the registration error estimation.

26. The method according to claim 21, wherein when at least some of said markers are fiducial markers, said determining the position of at least three of said markers includes, for at least one marker, the method further comprises:
identifying said at least one marker within the field of view of said optical detection assembly, said optical detection assembly being attached to said portable unit;
for each of at least one registration position, determining respective position related information of each of said at least one marker being within the field of view of said optical detection assembly; and
determining the position of each of said at least one marker in said reference coordinate system according to the respective position and orientation of said portable unit in each of said at least one registration position and said position related information respective of each of said at least one marker.

27. The method according to claim 26, further including directing said user to move in a direction where additional markers would be within the field of view of said optical detection assembly.

28. The method according to claim 26, wherein said position related information is at least one of:
a direction from said portable unit toward said marker;
at least two directions from said portable unit toward said marker; or
a direction and a distance from said portable unit toward said marker.

29. The method according to claim 21, wherein at least some of said markers are anatomical landmarks.

30. The method according to claim 29, wherein said determining the position of at least some of said anatomical markers is performed with a tracked pointer.

* * * * *